US010687528B2

(12) United States Patent
Fevre et al.

(10) Patent No.: US 10,687,528 B2
(45) Date of Patent: Jun. 23, 2020

(54) ANTIMICROBIAL POLYMERS WITH ENHANCED FUNCTIONALITIES

(71) Applicants: International Business Machines Corporation, Armonk, NY (US); Agency for Science, Technology and Research, Connexis (SG)

(72) Inventors: Mareva B. Fevre, San Jose, CA (US); James L. Hedrick, Pleasanton, CA (US); Nathaniel H. Park, San Jose, CA (US); Victoria A. Piunova, Los Gatos, CA (US); Pang Kern Jeremy Tan, Singapore (SG); Chuan Yang, Hillington Green (SG); Yi Yan Yang, Singapore (SG)

(73) Assignees: INTERNATIONAL BUSINESS MACHINES CORPORATION, Armonk, NY (US); AGENCY FOR SCIENCE, TECHNOLOGY AND RESEARCH, Connexis (SG)

(*) Notice: Subject to any disclaimer, the term of this patent is extended or adjusted under 35 U.S.C. 154(b) by 120 days.

(21) Appl. No.: 15/839,397

(22) Filed: Dec. 12, 2017

(65) Prior Publication Data
US 2019/0174753 A1 Jun. 13, 2019

(51) Int. Cl.
| | | |
|---|---|---|
| *A01N 25/04* | (2006.01) | |
| *A01N 27/00* | (2006.01) | |
| *A01N 33/04* | (2006.01) | |
| *A01N 43/08* | (2006.01) | |
| *A01N 37/02* | (2006.01) | |
| *A01N 37/20* | (2006.01) | |
| *A01N 47/12* | (2006.01) | |
| *A01N 33/12* | (2006.01) | |
| *A61K 8/84* | (2006.01) | |
| *A61Q 17/00* | (2006.01) | |

(52) U.S. Cl.
CPC ............ *A01N 33/04* (2013.01); *A01N 25/04* (2013.01); *A01N 27/00* (2013.01); *A01N 33/12* (2013.01); *A01N 37/02* (2013.01); *A01N 37/20* (2013.01); *A01N 43/08* (2013.01); *A01N 47/12* (2013.01); *A61K 8/84* (2013.01); *A01N 2300/00* (2013.01); *A61Q 17/005* (2013.01)

(58) Field of Classification Search
CPC ........ A01N 25/04; A01N 27/00; A01N 33/04; A01N 43/08
See application file for complete search history.

(56) References Cited

U.S. PATENT DOCUMENTS

| | | | |
|---|---|---|---|
| 3,632,623 A | 1/1972 | Becke et al. | |
| 4,013,507 A | 3/1977 | Rembaum | |
| 4,032,596 A | 6/1977 | Uffner et al. | |
| 4,094,827 A | 6/1978 | McEntire | |
| 4,166,894 A | 9/1979 | Schaper | |
| 4,348,536 A | 9/1982 | Blahak et al. | |
| 4,698,391 A | 10/1987 | Yacobucci et al. | |
| 4,794,031 A | 12/1988 | Leir et al. | |
| 4,883,655 A | 11/1989 | Login et al. | |
| 5,419,897 A | 5/1995 | Drake et al. | |
| 5,681,862 A | 10/1997 | Hollis et al. | |
| 6,767,549 B2 | 7/2004 | Mandeville, III et al. | |
| 6,955,806 B2 | 10/2005 | Fitzpatrick et al. | |
| 8,541,477 B2 | 9/2013 | Alabdulrahman et al. | |
| 2006/0002889 A1 | 1/2006 | Fitzpatrick | |
| 2007/0025954 A1 | 2/2007 | Fitzpatrick et al. | |
| 2007/0106061 A1 | 5/2007 | Zollinger et al. | |
| 2012/0202979 A1 | 8/2012 | Wu | |
| 2013/0281515 A1 | 10/2013 | Coady et al. | |
| 2014/0275469 A1 | 9/2014 | Dhal et al. | |
| 2015/0038392 A1 | 2/2015 | Scheuing et al. | |
| 2016/0374335 A1 | 12/2016 | Chan et al. | |
| 2016/0375150 A1 | 12/2016 | Wu | |

FOREIGN PATENT DOCUMENTS

| | | |
|---|---|---|
| CN | 1192649 A | 9/1998 |
| CN | 1254334 A | 5/2000 |
| CN | 1518621 A | 8/2004 |
| CN | 101426507 A | 5/2009 |
| CN | 101646728 A | 2/2010 |
| CN | 105482105 A | 4/2016 |
| GB | 2 000 164 A | 1/1979 |
| JP | H03255139 A | 11/1991 |
| JP | 2004-224734 A | 8/2004 |
| JP | 2008214529 A | 9/2008 |
| WO | 97/02744 A1 | 1/1997 |

(Continued)

OTHER PUBLICATIONS

Wettig (Physical Chemistry Chemical Physics, pp. 871-877, published 2007) (Year: 2007).*
Shen et al. (Chem. Mater. Published 2003, pp. 4046-4051). (Year: 2003).*
Wang et al. (Phys. Chem. Chem. Phys. Published 2013, pp. 20510-20516) (Year: 2013).*
International Search Report and Written Opinion received for PCT Application Serial No. PCT/IB2018/059624 dated Apr. 17, 2019, 8 pages.

(Continued)

*Primary Examiner* — Alma Pipic

(74) *Attorney, Agent, or Firm* — Amin, Turocy & Watson, LLP

(57) ABSTRACT

Techniques regarding ionene and/or polyionene compositions with antimicrobial functionalities are provided. For example, one or more embodiments can comprise a chemical compound, which can comprise an ionene unit. The ionene unit can comprise a cation distributed along a degradable backbone. The degradable backbone can comprise a norspermidine structure having a carbonyl group. Also, the ionene unit can have antimicrobial functionality.

2 Claims, 13 Drawing Sheets

(56) References Cited

FOREIGN PATENT DOCUMENTS

| WO | 98/54140 A1 | 12/1998 |
|---|---|---|
| WO | 02/080939 A2 | 10/2002 |
| WO | 02/099192 A2 | 12/2002 |
| WO | 2016/178634 A1 | 11/2016 |
| WO | 2016/186581 A1 | 11/2016 |
| WO | 2016/209732 A1 | 12/2016 |

OTHER PUBLICATIONS

Non-Final Office Action received for U.S. Appl. No. 15/839,388 dated Jul. 10, 2019, 52 pages.
Murakami et al., "Syntheses of Macrocyclic Enzyme Models, Part 4. Preparation and Characterization of Cationic Octopus Azaparacyclophanes", Organic and Bio-Organic Chemistry, Journal of the Chemical Society, Perkin Transactions 1, Issue 11, Jan. 1, 1981, pp. 2800-2808.
Non-Final Office Action received for U.S. Appl. No. 15/839,199 dated Jun. 26, 2019, 66 pages.
Tiecco et al., "Biocidal and inhibitory activity screening of de novo synthesized surfactants against two eukaryotic and two prokaryotic microbial species", Science Direct, Colloids and Surfaces B: Biointerfaces, vol. 111, Nov. 71, 2013, 35 pages.
Non-Final Office Action received for U.S. Appl. No. 15/839,402 dated Jun. 26, 2019, 56 pages.
Odagi et al., "Origin of Stereocontrol in Guanidine-Bisurea Bifunctional Organocatalyst That Promotes α-Hydroxylation of Tetralone-Derived β-Ketoesters: Asymmetric Synthesis of β- and γ-Substituted Tetralone Derivatives via Organocatalytic Oxidative Kinetic Resolution", Journal of the American Chemical Society, Jan. 2015, pp. 1909-1915.
Magri et al., "Rethinking the old antiviral drug moroxydine: Discovery of novel analogues as anti-hepatitis C virus (HCV) agents", Bioorganic and Medicinal Chemistry Letters, vol. 25, No. 22, Nov. 2015, pp. 5372-5376.
Non-Final Office Action received for U.S. Appl. No. 15/839,415 dated Jul. 10, 2019, 29 pages.
International Search Report and Written Opinion received for PCT Application Serial No. PCT/IB2018/059621 dated Apr. 10, 2019, 8 pages.
Liu, et al., Highly potent antimicrobial polyionenes with rapid killing kinetics, skin biocompatibility and in vivo bactericidal activity, Biomaterials, 2017, pp. 36-48, vol. 127.
Williams, et al., Recent advances in the synthesis and structure-property relationships of ammonium ionenes, Progress in Polymer Science, 2009, pp. 762-782, vol. 34.
Narita, et al., Effects of charge density and hydrophobicity of ionene polymer on cell binding and viability, Colloid Polym. Sci, 2000, pp. 884-887.
Mattheis, et al., Closing One of the Last Gaps in Polyionene Compositions: Alkyloxyethylammonium Ionenes as Fast-Acting Biocides, Macromolecular Bioscience, 2012, pp. 341-349, vol. 12.
Strassburg, et al., Nontoxic, Hydrophilic Cationic Polymers—Identified as Class of Antimicrobial Polymers, Macromolecular Bioscience, 2015, pp. 1710-1723, vol. 15.
Mayr, et al., Antimicrobial and Hemolytic Studies of a Series of Polycations Bearing Quaternary Ammonium Moieties: Structural and Topological Effects, International Journal of Molecular Sciences, 2017, 8 pages, vol. 18, No. 303.
Tamami, Synthesis and Characterization of Ammonium Ionenes Containing Hydrogen Bonding Functionalities, Dec. 6, 2012, 108 pages, Virginia Polytechnic Institute and State University.

Brown et al., The Structure Activity Relationship of Urea Derivatives as Anti-Tuberculosis Agents, Bioorg Med Chem. Sep. 15, 2011, pp. 5585-5595 vol. 19, No. 18.
Williams, Influence of Electrostatic Interactions and Hydrogen Bonding on the Thermal and Mechanical Properties of Step-Growth Polymers, Oct. 21, 2008, 375 pages, Virginia Polytechnic Institute and State University.
International Search Report and Written Opinion received for PCT Application Serial No. PCT/IB2018/059622, dated Mar. 28, 2019, 9 pages.
International Search Report and Written Opinion received for PCT Application Serial No. PCT/IB2018/059626, dated Apr. 15, 2019, 8 pages.
International Search Report and Written Opinion received for PCT Application Serial No. PCT/IB2018/059620, dated Mar. 27, 2019, 11 pages.
Final Office Action received for U.S. Appl. No. 15/839,199 dated Sep. 26, 2019, 25 pages.
Non-Final Office Action received for U.S. Appl. No. 15/839,270 dated Sep. 16, 2019, 70 pages.
Notice of Allowance received for U.S. Appl. No. 15/839,402 dated Oct. 24, 2019, 113 pages.
Chahboune et al., "Application of liquid chromatography/electrospray ionization tandem mass spectrometry for the elucidation of hydroxyl radical oxidation of metsulfuron methyl and related sulfonylurea pesticide products: evidence for the triazine skeleton scission", Rapid Communications in Mass Spectrometry, vol. 29, Sep. 2015, pp. 1370-1380.
Rafqah et al., "Kinetics and mechanism of the degradation of the pesticde metsulfuron methyl induced by excitation of iron(III) aqua complexes in aqueous solutions: steady state and transient absorption spectroscopy studies", Photochem. Photobial. Sci., vol. 3, 2004, pp. 296-304.
Si et al., "Leaching and degradation of ethametsulfuron-methyl in soil", Cehmosphere, vol. 60, 2005, pp. 601-609.
Li-Feng et al., "Biodegradation of Ethametsulfuron-Methyl by Pseudomonas sp. SW4 Isolated from Contaminated Soil", Curr Microbial, vol. 55, 2007, pp. 420-426.
Non-Final Office Action received for U.S. Appl. No. 15/839,410 dated Oct. 31, 2019, 41 pages.
Final Office Action received for U.S. Appl. No. 15/839,415 dated Nov. 6, 2019, 29 pages.
Advisory Action received for U.S. Appl. No. 15/839,199, dated Nov. 19, 2019, 16 pages.
Non-Final Office Action received for U.S. Appl. No. 15/839,199 dated Dec. 26, 2019, 156 pages.
Haque et al., Synthesis, Characterization, and Crystal Structures of Bis-Imidazolium Salts and Respective Dinuclear Ag(I) N-Heterocyclic Carbene Complexes: In Vitro Anticancer Studies against "Human Colon Cancer" and "Breast Cancer", Hindawi Publishing Corporation Journal of Chemistry, 2013, 11 pages.
Wynne et al., "Synthesis and Development of a Multifunctional Self-Decontaminating Polyurethane Coating", Applied Materials and Interfaces, 2011, pp. 2005-2011.
Oi'Khovik et al., "Synthesis, Antimicrobial and Antifungal Activity of Double Quaternary Alnmonium Salts of Biphenyls", Russian Journal of General Chemistry, vol. 83, No. 2, 2013, pp. 329-335.
Jones et al., ortlo Substitution Rearrangement vs. β)- Elimination of Quaternary Ammonium Ion-Alcohols and Methyl Ether with Excess Sodium Amide, vol. 27 ,1962, pp. 806-814.
Menger et al., "Synthesis and Properties of Nine New Polyhydroxylated Surfactants", Langmuir, vol. 12, No. 6, 1996, pp. 1471-1473.
Final Office Action received for U.S. Appl. No. 15/839,388 dated Dec. 5, 2019, 43 pages.
Non-Final Office Action received for U.S. Appl. No. 15/839,410 dated Apr. 22, 2020, 38 pages.

* cited by examiner

- 302 — COVALENTLY BONDING A HYDROXYL GROUP TO AN AMINO GROUP OF AN AMINE MONOMER TO FORM A PROTECTED AMINE MONOMER, THE PROTECTED AMINE MONOMER COMPRISING A BACKBONE, AND THE BACKBONE COMPRISING A NORSPERMIDINE STRUCTURE, WHEREIN THE HYDROXYL GROUP PROTECTS THE AMINO GROUP FROM POLYMERIZATION

- 304 — POLYMERIZING THE PROTECTED AMINE MONOMER WITH AN ELECTROPHILE TO FORM A HYDROXYL IONENE UNIT, THE HYDROXYL IONENE UNIT COMPRISING A CATION DISTRIBUTED ALONG THE BACKBONE

- 306 — DEPROTECTING THE HYDROXYL IONENE UNIT TO FORM AN IONENE UNIT, THE DEPROTECTING COMPRISING DEBONDING THE HYDROXYL GROUP FROM THE AMINO GROUP

| | 1102 | 1104 | 1106 | 1108 | 1110 |
|---|---|---|---|---|---|
| Ionene Composition | SA (µg/mL) | EC (µg/mL) | PA (µg/mL) | CA (µg/mL) | |
| First Ionene Composition 408 | 4 | 16 | 8 | 1 | |
| Second Ionene Composition 702 | 4 | 16 | 16 | 1 | |
| Fifth Ionene Compostion | 16 | 31 | 125 | 2 | |
| Sixth Ionene Composition | 8 | 63 | 63 | 1 | |

```
┌─────────────────────────────────────────────────────┐
│ CONTACTING A PATHOGEN WITH A POLYMER, THE POLYMER   │
│ COMPRISING AN IONENE UNIT HAVING A CATION AND AN    │── 1302
│ AMIDE GROUP, THE CATION AND THE AMIDE GROUP         │
│ DISTRIBUTED ALONG A BACKBONE, THE BACKBONE          │
│ COMPRISING A NORSPERMIDINE STRUCTURE                │
└─────────────────────────────────────────────────────┘
                            │
                            ▼
┌─────────────────────────────────────────────────────┐
│ ELECTROSTATICALLY DISRUPTING A MEMBRANE OF THE      │── 1304
│ PATHOGEN UPON CONTACTING THE PATHOGEN WITH THE      │
│ POLYMER                                             │
└─────────────────────────────────────────────────────┘
```

US 10,687,528 B2

ANTIMICROBIAL POLYMERS WITH ENHANCED FUNCTIONALITIES

BACKGROUND

The subject disclosure relates to one or more antimicrobial polymers with enhanced functionalities, and more specifically, to one or more antimicrobial ionenes and/or polyionenes with enhanced functionalities, such as increased degradability and/or intracellular mobility.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding polyionenes with antimicrobial functionality are described.

According to an embodiment, a chemical compound is provided. The chemical compound can comprise an ionene unit that can comprise a nitrogen cation distributed along a molecular backbone. The molecular backbone can comprise a norspermidine structure. Also, the ionene unit can have antimicrobial functionality.

According to an embodiment, a chemical compound is provided. The chemical compound can comprise an ionene unit that can comprise a cation distributed along a degradable backbone. The degradable backbone can comprise a norspermidine structure having a carbonyl group. Also, the ionene unit can have antimicrobial functionality.

According to an embodiment, a chemical compound is provided. The chemical compound can comprise an ionene unit that can comprise a cation distributed along a molecular backbone. The molecular backbone can comprise a norspermidine structure having a carbamate functional group. Also, the ionene unit can have antimicrobial functionality.

According to an embodiment, a method is provided. The method can comprise dissolving an ionene unit with an oxidizing agent in a solvent. The ionene unit can comprise a cation distributed along a backbone. The backbone can comprise a norspermidine structure. The method can also comprise oxidizing the ionene unit with the oxidizing agent to form a degradable ionene unit. The oxidizing can form a carbonyl group along the backbone. Also, the degradable ionene unit can have antimicrobial functionality.

According to an embodiment, a method is provided. The method can comprise dissolving an ionene unit with a carbonate in a solvent. The ionene unit can comprise a cation distributed along a backbone. The backbone can comprise a norspermidine structure. The method can also comprise polymerizing the ionene unit with the carbonate to form a functionalized ionene unit. The polymerizing can form a carbamate functional group covalently bonded to the backbone. Also, the functionalized ionene unit can have antimicrobial functionality.

BRIEF DESCRIPTION OF THE DRAWINGS

FIG. 3 illustrates a flow diagram of an example, non-limiting method that can facilitate generating one or more ionene units in accordance with one or more embodiments described herein.

FIG. 13 illustrates a flow diagram of an example, non-limiting method that can facilitate killing of a pathogen with one or more ionene compositions in accordance with one or more embodiments described herein.

DETAILED DESCRIPTION

Figure 1A:
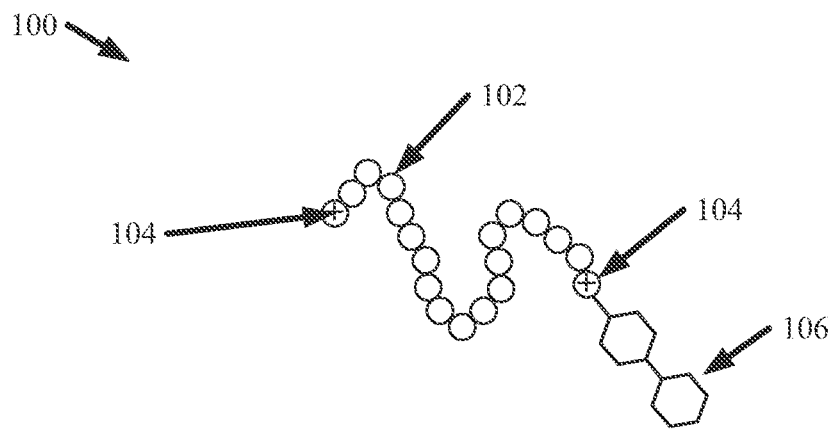
FIG. 1A illustrates a diagram of an example, non-limiting ionene unit in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The discovery and refinement of antibiotics was one of the crowning achievements in the $20^{th}$ century that revolutionized healthcare treatment. For example, antibiotics such as penicillin, ciprofloxacin and, doxycycline can achieve microbial selectivity through targeting and disruption of a specific prokaryotic metabolism, while concurrently, remaining benign toward eukaryotic cells to afford high selectivity. If properly dosed, they could eradicate infection. Unfortunately, this therapeutic specificity of antibiotics also leads to their undoing as under-dosing (incomplete kill) allows for minor mutative changes that mitigate the effect of the antibiotic leading to resistance development. Consequently, nosocomial infections, caused by medication-resistant microbes such as methicillin-resistant *Staphylococcus aureus* (MRSA), multi-medication-resistant *Pseudomonas aeruginosa* and vancomycin-resistant Enterococci (VRE) have become more prevalent. An added complexity is the pervasive use of antimicrobial agents in self-care products, sanitizers and hospital cleaners etc, including anilide, bisphenols, biguanides and quaternary ammonium compounds, where a major concern is the development of cross- and co-resistance with clinically used antibiotics, especially in a hospital setting. Another unfortunate feature with triclosan, for example, is its cumulative and persistent effects in the skin. Moreover, biofilms have been associated with numerous nosocomial infections and implant failure, yet the eradication of biofilms is an unmet challenge to this date. Since antibiotics are not able to penetrate through extracellular polymeric substance that encapsulates bacteria in the biofilm, further complexities exist that lead to the development of medication resistance.

However, polymers having a cationic charge can provide electrostatic disruption of the bacterial membrane interaction. Furthermore, cationic polymers are readily made amphiphilic with addition of hydrophobic regions permitting both membrane association and integration/lysis. The amphiphilic balance has shown to play an important effect not only in the antimicrobial properties but also in the hemolytic activity. Many of these antimicrobial polymers show relatively low selectivity as defined by the relative toxicity to mammalian cells or hemolysis relative to pathogens.

As used herein, the term "ionene" can refer to a polymer unit, a copolymer unit, and/or a monomer unit that can comprise a nitrogen cation and/or a phosphorus cation distributed along, and/or located within, a molecular backbone, thereby providing a positive charge. Example nitrogen cations include, but are not limited to: quaternary ammonium cations, protonated secondary amine cations, protonated tertiary amine cations, and/or imidazolium cations. Example, phosphorus cations include, but are not limited to: quaternary phosphonium cations, protonated secondary phosphine cations, and protonated tertiary phosphine cations. As used herein, the term "molecular backbone" can refer to a central chain of covalently bonded atoms that form the primary structure of a molecule. In various embodiments described herein, side chains can be formed by bonding one or more functional groups to a molecular backbone. As used herein, the term "polyionene" can refer to a polymer that can comprise a plurality of ionenes. For example, a polyionene can comprise a repeating ionene.

FIG. 1A illustrates a diagram of an example, non-limiting ionene unit 100 in accordance with one or more embodiments described herein. The ionene unit 100 can comprise a molecular backbone 102, one or more cations 104, and/or one or more hydrophobic functional groups 106. In various embodiments, an ionene and/or a polyionene described herein can comprise the ionene unit 100. For example, a polyionene described herein can comprise a plurality of ionenes bonded together, wherein the bonded ionenes can have a composition exemplified by ionene unit 100.

Figure 1B:
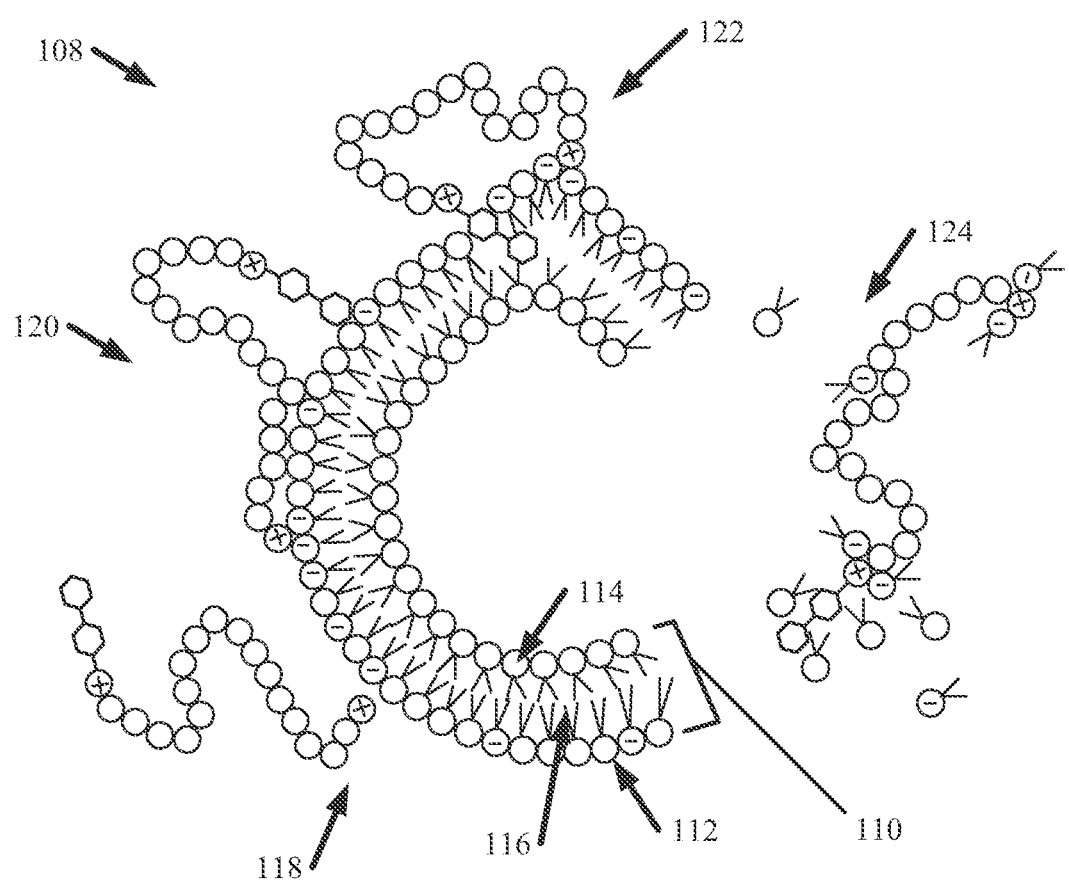
FIG. 1B illustrates a diagram of an example, non-limiting lysis process that can be performed by one or more ionene units in accordance with one or more embodiments described herein.

The molecular backbone 102 can comprise a plurality of covalently bonded atoms (illustrated as circles in FIGS. 1A and 1B). The atoms can be bonded in any desirable formation, including, but not limited to: chain formations, ring formations, and/or a combination thereof. The molecular backbone 102 can comprise one or more chemical structures including, but not limited to: alkyl structures, aryl structures, alkane structures, aldehyde structures, ester structures, carboxyl structures, carbonyl structures, amine structures, amide structures, phosphide structures, phosphine structures, a combination thereof, and/or the like. One of ordinary skill in the art will recognize that the number of atoms that can comprise the molecular backbone can vary depending of the desired function of the ionene unit 100. For example, while nineteen atoms are illustrated in FIG. 1A, a molecular backbone 102 that can comprise dozens, hundreds, and/or thousands of atoms is also envisaged.

Located within the molecular backbone 102 are one or more cations 104. As described above, the one or more cations 104 can comprise nitrogen cations and/or phosphorous cations. The cations 104 can be distributed along the molecular backbone 102, covalently bonded to other atoms within the molecular backbone 102. In various embodiments, the one or more cations 104 can comprise at least a portion of the molecular backbone 102. One of ordinary skill in the art will recognize that the number of a cations 104 that can comprise the ionene unit 100 can vary depending of the desired function of the ionene unit 100. For example, while two cations 104 are illustrated in FIG. 1A, an ionene unit 100 that can comprise dozens, hundreds, and/or thousands of cations 104 is also envisaged. Further, while FIG. 1A illustrates a plurality of cations 104 evenly spaced apart, other configurations wherein the cations 104 are not evenly spaced apart are also envisaged. Also, the one or more cations 104 can be located at respective ends of the molecular backbone 102 and/or at intermediate portions of the molecular backbone 102, between two or more ends of the molecular backbone 102. The one or more cations 104 can provide a positive charge to one or more locations of the ionene unit 100.

The one or more hydrophobic functional groups 106 can be bonded to the molecular backbone 102 to form a side chain. The one or more of the hydrophobic functional groups 106 can be attached to the molecular backbone 102 via bonding with a cation 104. Additionally, one or more hydrophobic functional groups 106 can be bonded to an electrically neutral atom of the molecular backbone 102. The ionene unit 100 can comprise one or more hydrophobic functional groups 106 bonded to: one or more ends of the molecular backbone 102, all ends of the molecular backbone 102, an intermediate portion (e.g., a portion between two ends) of the molecular backbone 102, and/or a combination thereof.

While a biphenyl group is illustrated in FIG. 1A as the hydrophobic functional group 106, other functional groups that are hydrophobic are also envisaged. Example, hydrophobic functional groups 106 can include, but are not limited to: alkyl structures, aryl structures, alkane structures, aldehyde structures, ester structures, carboxyl structures, carbonyl structures, carbonate structures, alcohol structures, a combination thereof, and/or the like. In various embodiments, the one or more hydrophobic functional groups 106 can comprise the same structure. In other embodiments, one or more of the hydrophobic functional groups 106 can comprise a first structure and one or more other hydrophobic functional groups 106 can comprise another structure.

FIG. 1B illustrates a diagram of an example, non-limiting lysis process 108 that can be facilitated by the ionene unit 100 in accordance with one or more embodiments described herein. Repetitive description of like elements employed in other embodiments described herein is omitted for sake of brevity. The lysis process 108 can comprise a plurality of stages, which can collectively comprise an attack mechanism that can be performed by the ionene unit 100 against a pathogen cell. Example pathogen cells can include, but are not limited to: Gram-positive bacteria cells, Gram-negative bacteria cells, fungi cells, and/or yeast cells.

The target pathogen cell can comprise a membrane having a phospholipid bilayer 110. In various embodiments, the membrane can be an extracellular matrix. The phospholipid bilayer 110 can comprise a plurality of membrane molecules 112 covalently bonded together, and the membrane molecules 112 can comprise a hydrophilic head 114 and one or more hydrophobic tails 116. Further, one or more of the plurality of membrane molecules 112 can be negatively charged (as illustrated in FIG. 1B with a "−" symbol).

At 118, electrostatic interaction can occur between the positively charged cations 104 of the ionene unit 100 and one or more negatively charged membrane molecules 112. For example, the negative charge of one or more membrane molecules 112 can attract the ionene unit 100 towards the membrane (e.g., the phospholipid bilayer 110). Also, the electrostatic interaction can electrostatically disrupt the integrity of the membrane (e.g., phospholipid bilayer 110). Once the ionene unit 100 has been attracted to the membrane (e.g., phospholipid bilayer 110), hydrophobic membrane integration can occur at 120. For example, at 120 one or more hydrophobic functional groups 106 of the ionene unit 100 can begin to integrate themselves into the phospholipid bilayer 110. While the positively charged portions of the ionene unit 100 are attracted, and electrostatically disrupting, one or more negatively charged membrane molecules 112 (e.g., one or more hydrophilic heads 114), the one or more hydrophobic functional groups 106 can insert themselves between the hydrophilic heads 114 to enter a hydrophobic region created by the plurality of hydrophobic tails 116.

As a result of the mechanisms occurring at 118 and/or 120, destabilization of the membrane (e.g., the phospholipid bilayer 110) can occur at 122. For example, the one or more hydrophobic functional groups 106 can serve to cleave one or more negatively charged membrane molecules 112 from adjacent membrane molecules 112, and the positively charged ionene unit 100 can move the cleaved membrane segment (e.g., that can comprise one or more negatively charged membrane molecules 112 and/or one or more neutral membrane molecules 112 constituting a layer of the phospholipid bilayer 110) away from adjacent segments of the membrane (e.g., adjacent segments of the phospholipid bilayer 110). As cleaved segments of the membrane (e.g., the phospholipid bilayer 110) are pulled away, they can fully detach from other membrane molecules 112 at 124, thereby forming gaps in the membrane (e.g., the phospholipid bilayer 110). The formed gaps can contribute to lysis of the subject pathogen cell. In various embodiments, a plurality of ionene units 100 can perform the lysis process 108 on a cell simultaneously. Furthermore, the ionene units 100 participating in a lysis process 108 need not perform the same stages of the attack mechanism at the same time.

Figure 2:
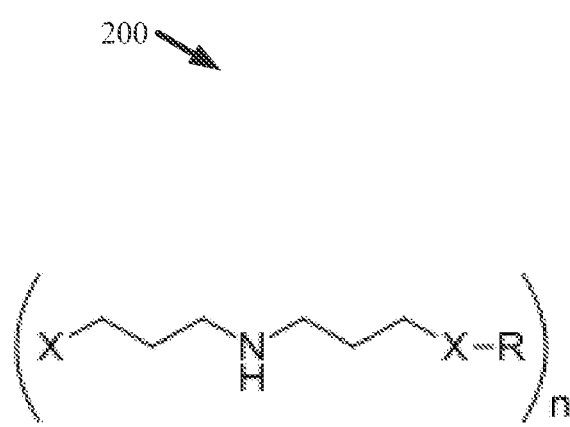
FIG. 2 illustrates a diagram of an example, non-limiting chemical formula that can characterize one or more ionene units in accordance with one or more embodiments described herein.

FIG. 2 illustrates a diagram of an example, non-limiting chemical formula 200 that can characterize the structure of an ionene unit 100 in accordance with one or more embodiments described herein. Repetitive description of like elements employed in other embodiments described herein is omitted for sake of brevity. In various embodiments, the ionene units 100 characterized by chemical formula 200 can be covalently bonded together to form a polymer (e.g., a homopolymer, an alternating copolymer, and/or a random copolymer).

As shown in FIG. 2, an ionene unit 100 characterized by chemical formula 200 can comprise a molecular backbone 102. Further, the molecular backbone 102 can comprise one or more norspermidine structures. In various embodiments, the ionene unit 100 characterized by chemical formula 200 can be derived from 3.3'-iminobis(N, N-dimethyl propylamine), wherein the one or more norspermidine structures can be derived from the 3.3'-iminobis(N, N-dimethyl propylamine). However, one or more embodiments of chemical formula 200 can comprise a norspermidine structure derived from one or more molecules other than 3.3'-iminobis(N, N-dimethyl propylamine).

The "X" in FIG. 2 can represent the one or more cations 104. For example, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. As shown in FIG. 2, in various embodiments, an ionene unit 100 characterized by chemical formula 200 can comprise cations 104 (e.g., represented by "X") at a plurality of locations along the molecular backbone 102. For example, cations 104 can be located at either end of the molecular backbone 102 (e.g., as illustrated in FIG. 2). However, in one or more embodiments of chemical formula 200, the molecular backbone 102 can comprise less or more cations 104 than the two illustrated in FIG. 2.

Further, the "R" shown in FIG. 2 can represent the one or more hydrophobic functional groups 106 in accordance with the various embodiments described herein. For example, the one or more hydrophobic functional groups 106 can comprise one or more alkyl groups and/or one or more aryl groups. For instance, the one or more hydrophobic functional group 106 can be derived from one or more dialkyl halides. The one or more hydrophobic functional groups 106 (e.g., represented by "R" in FIG. 2) can be covalently bonded to one or more of the cations 104 (e.g., represented by "X" in FIG. 2) and/or the molecular backbone 102, which can comprise the one or more cations 104 (e.g., represented by "X" in FIG. 2) and/or one or more norspermidine structures. In addition, the "n" shown in FIG. 2 can represent an integer greater than or equal to one and less than or equal to one thousand. In one or more embodiments, chemical formula 200 can characterize ionene and/or polyionene compositions having a molecular weight greater than or equal to 3,000 grams per mole (g/mol) and less than or equal to 10,000 g/mol (e.g., greater than or equal to 4,000 g/mol and less than or equal to 7,000 g/mol).

FIG. 3 illustrates a flow diagram of an example, non-limiting method 300 that can facilitate generating one or more ionene units 100 (e.g., characterized by chemical formula 200) in accordance with one or more embodiments described herein. Repetitive description of like elements employed in other embodiments described herein is omitted for sake of brevity.

At 302, the method 300 can comprise covalently bonding one or more hydroxyl groups to one or more amino groups of an amine monomer to protect said one or more amino groups from subsequent polymerizations. The one or more amine monomers can comprise a molecular backbone 102 having one or more norspermidine structures. For example, the one or more amine monomers can be a tri-amines. Additionally, the one or more amino groups can be primary amino groups and/or secondary amino groups. In one or more embodiments, the amino group can be a secondary amino group. The bonding at 302 can form one or more hydroxyl functional groups covalently bonded to the one or more amino groups (e.g., a secondary amino group of the subject amine monomer). Thus, the bonding at 302 can subject one or more amino groups to alkylation (e.g., transforming one or more primary amino groups into one or more secondary amino group and/or one or more secondary amino groups into one or more tertiary amino group), thereby bonding one or more hydroxyl functional groups to the amine monomer's molecular backbone 102 and/or protecting one or more amino groups comprising the molecular backbone 102 from future polymerizations.

The bonding at 302 can be facilitated by dissolving the one or more amine monomers with a formaldehyde derivative (e.g., acetone) in a solvent. For example, the formaldehyde derivative can comprise an acetyl group. Further, the solvent can be an organic solvent. Additionally, the solvent can be an aprotic solvent, a dipolar solvent, and/or an alcohol. Example solvents can include but are not limited to: dimethyl formamide ("DMF"), methanol, a combination thereof, and/or the like.

At 304, the method 300 can comprise polymerizing the one or more protected amine monomers with one or more electrophiles to form one or more hydroxyl ionene units 100 (e.g., an ionene unit 100 comprising one more hydroxyl functional groups). The one or more hydroxyl ionene units 100 can comprise one or more cations 104 distributed along the molecular backbone 102. For example, the one or more cations 104 can be protonated secondary amine cations, protonated tertiary amine cations, quaternary ammonium cations, and/or imidazolium cations.

The one or more electrophiles can comprise, for example, one or more alkyl halides (e.g., dialkyl halides). For instance, the one or more electrophiles can comprise one or more dialkyl halides having chloride and/or bromide. Example electrophiles can include, but are not are not limited to: p-xylylene dichloride; 4,4'-bis(chloromethyl)biphenyl; 1,4-bis(bromomethyl)benzene; 4,4'-bis(bromomethyl)biphenyl; 1,4-bis(iodomethyl)benzene; 1,6-dibromohexane; 1,8-dibromooctane; 1,12-dibromododecane; 1,6-dichlorohexane; 1,8-dichlorooctane; a combination thereof; and/or the like.

The polymerizing at 304 can comprise an alkylation process and/or a quaternization process with the one or more electrophiles and/or one or more unprotected amino groups of the one or more protected amino monomers. For example, the one or more electrophiles can bond with one or more amino groups of the one or more protected amine monomers, which are not bonded to one or more hydroxyl functional groups, to form the one or more hydrophobic functional groups 106 and one or more cations 104. Thus, the polymerization at 304 can conduct a polymer-forming reaction and an installation of charge (e.g., forming one or more cations 104) simultaneously without a need of a catalyst. However, the hydroxyl groups formed at 302 can protect the one or more amino groups bonded to said hydroxyl groups from the alkylation and/or quaternization performed at 304. Therefore, the bonding at 302 and the polymerization at 304 can render one or more of the amino groups comprising the one or more amine monomers either positively charged (e.g., via alkylation and/or quaternization) or bonded to one or more hydroxyl functional groups (e.g., via alkylation).

At 306, the method 300 can comprise deprotecting the one or more hydroxyl ionene units 100, which can comprise the one or more cations 104, to form one or more ionene units 100 (e.g., characterized by chemical formula 200). The deprotecting at 306 can comprise debonding (e.g., removing) the one or more hydroxyl functional groups that could have been formed at 302, which could have protected one or more amino groups from the polymerization at 304. In other words, the one or more hydroxyl functional groups that could have be formed at 302 could have served to shield one or more amino groups from the cation 104 forming polymerization at 304. Post said polymerization at 304, one or more of the hydroxyl functional groups can be removed at 306 to facilitate bonding of other functional groups to the ionene unit 100 (e.g., characterized by chemical formula 200) formed by the method 300. The deprotecting at 306 can be facilitated by dissolving the hydroxyl ionene that can be formed at 304 with an acid in a solvent. For example, the solvent can comprise an alcohol.

The method 300 can generate one or more monomers comprising an ionene unit 100 (e.g., characterized by chemical formula 200). Additionally, the method 300 can covalently bond (e.g., at the polymerization at 304) multiple hydroxyl ionene units 100 together to form a polymer; thus, the method 300 (e.g., via the polymerization at 304 and/or the deprotecting at 306) can form a polymer (e.g., a homopolymer, an alternate copolymer, and/or a random copolymer). In one or more embodiments, method 300 can generate ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

For example, the ionene formed at 306 can comprise one or more embodiments of the ionene unit 100 and can be characterized by one or more embodiments of chemical formula 200. For instance, the ionene unit 100 formed at 306 can comprise a molecular backbone 102 that can comprise one or more cations 104 (e.g., represented by "X" in chemical formula 200), one or more norspermidine structures, and/or one or more hydrophobic functional groups 106 (e.g., represented by "R" in chemical formula 200). The one or more cations 104 can be nitrogen cations (e.g., protonated secondary amine cations, protonated tertiary amine cations, quaternary ammonium cations, imidazolium cations, and/or a combination thereof). Also, the one or more of the cations 104 can be bonded to one or more of the hydrophobic functional groups 106. Additionally, the ionene unit 100 can comprise a polyionene by repeating a number of times, as represented by "n" in chemical formula 200

(e.g., shown in FIG. 2), which can be an integer greater than or equal to one and less than or equal to one thousand.

Figure 4:
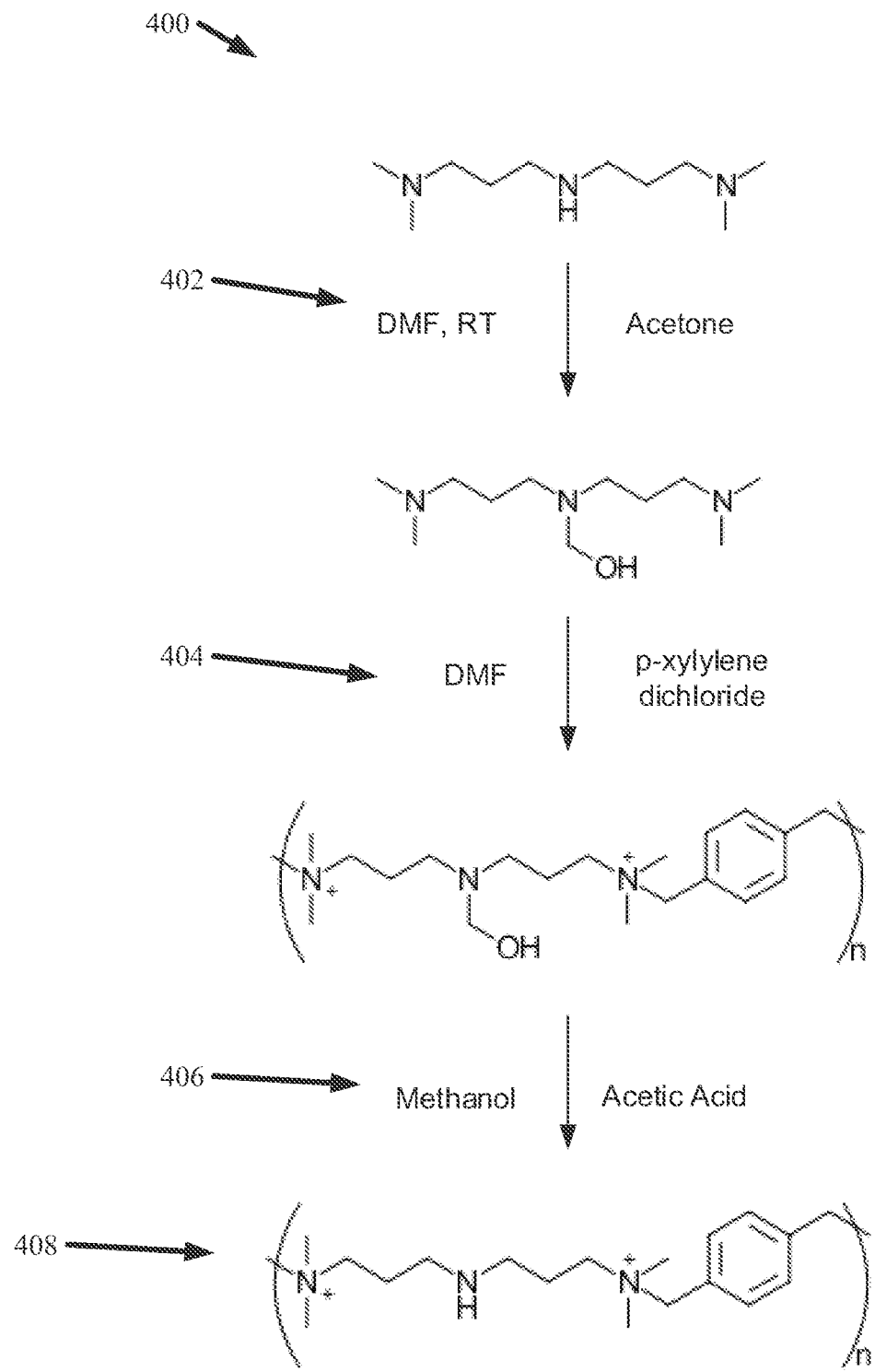
FIG. 4 illustrates a diagram of an example, non-limiting scheme that can depict generating one or more ionene units in accordance with one or more embodiments described herein.

FIG. 4 illustrates a diagram of an example, non-limiting scheme 400 that can depict generating one or more ionene units 100 (e.g., characterized by chemical formula 200) in accordance with one or more of the methods (e.g., method 300) described herein. Repetitive description of like elements employed in other embodiments described herein is omitted for sake of brevity. In scheme 400, "n" can represent a first integer greater than or equal to one and less than or equal to one thousand. Scheme 400 can exemplify one or more ionene units 100 characterized by chemical formula 200 and/or generated by method 300. While one or more particular amine monomers, oxidizing agents, solvents, electrophiles, and/or acids are depicted; additional embodiments of scheme 400 are also envisaged. For example, the principal mechanisms of scheme 400 can be applied to any amine monomer, oxidizing agent, solvent electrophile, and/or acid in accordance with the various features described herein (e.g., with reference to chemical formula 200 and/or method 300).

At 402, scheme 400 can depict covalently bonding one or more amine monomers (e.g., 3.3'-iminobis(N, N-dimethyl propylamine)) with one or more hydroxyl functional groups derived from one or more formaldehyde derivatives (e.g., acetone) in a solvent (e.g., DMF) at room temperature ("RT"). The covalent bonding at 402 can protect one or more amino groups of the one or more amine monomers (e.g., 3.3'-iminobis(N, N-dimethyl propylamine)) from subsequent polymerization. For example, 402 can comprise stirring the one or more amine monomers, the acetone, and the DMF at a temperature greater than or equal to 15 degrees Celsius (° C.) and less than or equal to 150° C. for a period of time greater than or equal to 8 hours and less than or equal to 72 hours (e.g., greater than or equal to 12 hours and less than or equal to 24 hours). Here, one or more hydroxyl functional groups can be covalently bonded to one or more amino groups (e.g., one or more secondary amino groups) of the one or more amine monomers (e.g., 3.3'-iminobis(N, N-dimethyl propylamine)).

At 404, scheme 400 can depict polymerizing the one or more protected amine monomers with one or more electrophiles (e.g., p-xylylene dichloride) in a solvent (e.g., DMF) to form a hydroxyl ionene unit 100. For example, 404 can comprise stirring the one or more protected amine monomers, the one or more electrophiles (e.g., p-xylylene dichloride), and/or the solvent (e.g., DMF) at a temperature greater than or equal to 15° C. and less than or equal to 150° C. for a period of time greater than or equal to 8 hours and less than or equal to 72 hours (e.g., greater than or equal to 12 hours and less than or equal to 24 hours). Here, the polymerization can comprise a quaternization of one or more amino groups of the one or more protected amine monomers with the one or more electrophiles (e.g., p-xylylene dichloride) to form one or more cations 104 and/or one or more hydrophobic functional groups 106 (e.g., bonded to one or more cations 104). Thus, the polymerization at 404 can comprise a polymer-forming reaction and an installation of charge (e.g., simultaneously). However, the one or more amino groups bonded to one or more hydroxyl functional groups could have been shielded from the quaternization at 404.

At 406, the scheme 400 can depict deprotecting the hydroxyl ionene unit 100 with an acid (e.g., acetic acid) in an alcohol solvent (e.g., methanol) to form an ionene unit 100, which can be characterized by chemical formula 200 (e.g., first ionene composition 408). For example, 406 can comprise stirring the one or more hydroxyl ionenes units, the acid (e.g., acetic acid), and/or the alcohol solvent (e.g., methanol) at a temperature greater than or equal to 15° C. and less than or equal to 150° C. for a period of time greater than or equal to 8 hours and less than or equal to 72 hours (e.g., greater than or equal to 12 hours and less than or equal to 24 hours). Here, one or more hydroxyl functional groups can be removed from the hydroxyl ionene unit 100 to form one or more ionene units 100, which can be characterized by chemical formula 200 (e.g., first ionene composition 408). For example, scheme 400 can generate a ionene monomer and/or a polyionene polymer (e.g., a homopolymer, an alternating copolymer, and/or a random copolymer). In one or more embodiments, scheme 400 can generate ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

Figure 5:
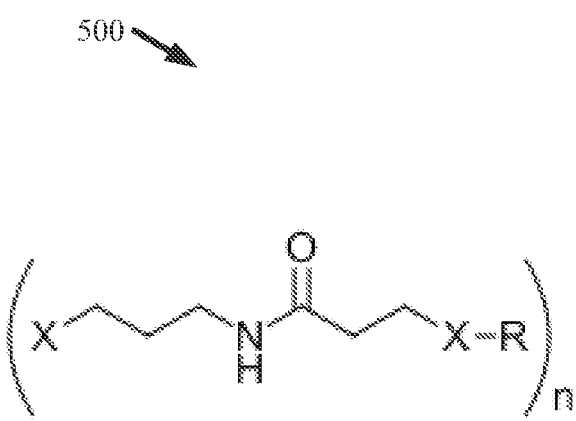
FIG. 5 illustrates a diagram of an example, non-limiting chemical formula that can characterize one or more ionene units in accordance with one or more embodiments described herein.

FIG. 5 illustrates another diagram of an example, non-limiting chemical formula 500 that can characterize the structure of an ionene unit 100 in accordance with one or more embodiments described herein. Repetitive description of like elements employed in other embodiments described herein is omitted for sake of brevity. In various embodiments, the ionene units 100 characterized by chemical formula 500 can be monomers and/or covalently bonded together to form a polymer (e.g., a homopolymer, an alternating copolymer, and/or a random copolymer).

As shown in FIG. 5, an ionene unit 100 characterized by chemical formula 500 can comprise a molecular backbone 102. Further, the molecular backbone 102 can comprise one or more norspermidine structures. In various embodiments, the ionene unit 100 characterized by chemical formula 500 can be derived from 3.3'-iminobis(N, N-dimethyl propylamine), wherein the one or more norspermidine structures can be derived from the 3.3'-iminobis(N, N-dimethyl propylamine). However, one or more embodiments of chemical formula 500 can comprise a norspermidine structure derived from one or more molecules other than 3.3'-iminobis(N, N-dimethyl propylamine). Additionally, the ionene unit 100 can comprise one or more carbonyl groups distributed along the molecular backbone 102. For example, one or more carbonyl groups can form an amide with one or more adjacent amino groups of the one or more norspermidine structures (e.g., as shown in FIG. 5).

The "X" in FIG. 5 can represent the one or more cations 104. For example, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. As shown in FIG. 5, in various embodiments, one or more ionene units 100 characterized by chemical formula 500 can comprise cations 104 (e.g., represented by "X") at a plurality of locations along the molecular backbone 102. For example, cations 104 can be located at either end of the molecular backbone 102 (e.g., as illustrated in FIG. 5). However, in one or more embodiments of chemical formula 500, the molecular backbone 102 can comprise less or more cations 104 than the two illustrated in FIG. 5.

Further, the "R" shown in FIG. 5 can represent the one or more hydrophobic functional groups 106 in accordance with the various embodiments described herein. For example, the one or more hydrophobic functional groups 106 can comprise one or more alkyl groups and/or one or more aryl groups. For instance, the one or more hydrophobic functional group 106 can be derived from one or more dialkyl halides. The one or more hydrophobic functional groups 106 (e.g., represented by "R" in FIG. 5) can be covalently bonded to one or more of the cations 104 (e.g., represented by "X" in FIG. 5) and/or the molecular backbone 102. The molecular backbone 102 can comprise the one or more cations 104 (e.g., represented by "X" in FIG. 5), one or more norspermidine structures, and/or one or more carbonyl groups. In addition, the "n" shown in FIG. 5 can represent an integer greater than or equal to one and less than or equal to one thousand. In one or more embodiments, chemical formula 500 can characterize ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

Figure 6:
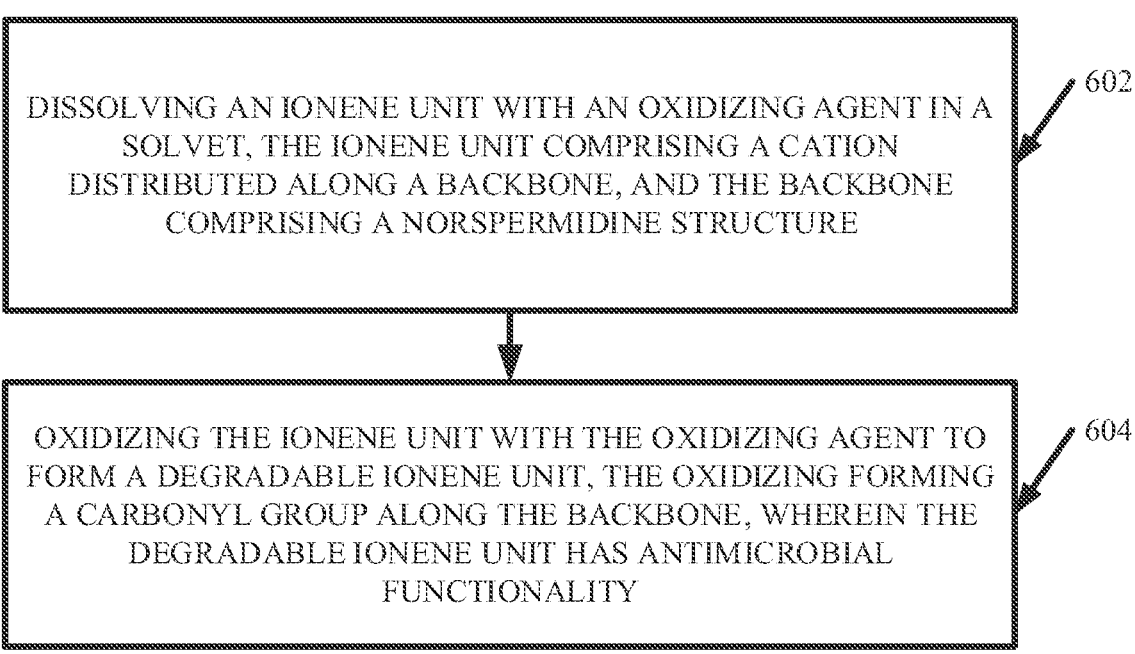
FIG. 6 illustrates a flow diagram of an example, non-limiting method that can facilitate generating one or more ionene units in accordance with one or more embodiments described herein.

FIG. 6 illustrates another flow diagram of an example, non-limiting method 600 that can facilitate generating one or more ionene units 100 (e.g., characterized by chemical formula 500) in accordance with one or more embodiments described herein. Repetitive description of like elements employed in other embodiments described herein is omitted for sake of brevity. In one or more embodiments, the one or more ionene units 100 utilized in method 600 can be prepared in accordance to the various features of method 300. However, one or more ionene units 100 prepared by alternative means can also be utilized in method 600.

At 602, the method 600 can comprise dissolving one or more ionene units 100 with an oxidizing agent in a solvent. The ionene unit 100 can be characterized by chemical formula 200. The ionene unit 100 can comprise one or more cations 104 distributed along a molecular backbone 102. For example, the one or more cations 104 can be protonated secondary amine cations, protonated tertiary amine cations, quaternary ammonium cations, and/or imidazolium cations. The molecular backbone 102 can comprise one or more norspermidine structures. For example, the ionene unit 100 can be a tri-amine. Additionally, one or more hydrophobic functional groups 106 can be covalently bonded to the molecular backbone 102 (e.g., bonded to the one or more cations 104).

The oxidizing agent can comprise one or more oxygens. For example, the oxidizing agent can be, but is not limited to, hydrogen peroxide. The solvent can comprise one or more alcohol groups. Additionally, the solvent can be an aprotic solvent, a dipolar solvent, and/or an alcohol. For example, the solvent can be, but is not limited to, methanol.

To facilitate the dissolving, the method 600 can further comprise stirring the one or more ionene units 100, the oxidizing agent, and/or the solvent at a temperature greater than or equal to 15° C. and less than or equal to 150° C. for a period of time greater than or equal to 8 hours and less than or equal to 72 hours (e.g., greater than or equal to 12 hours and less than or equal to 24 hours).

At 604, the method 600 can comprise oxidizing the ionene unit 100 with the oxidizing agent to form a polymer (e.g., a homopolymer, an alternating copolymer, and/or a random copolymer). The oxidizing at 604 can form one or more carbonyl groups along the molecular backbone 102 of the ionene unit 100 (e.g., characterized by chemical formula 200). For example, one or more carbon atoms comprising the ionene unit's 100 molecular backbone 102 can form a covalent double bond with an oxygen from the oxidizing agent. Thus, the polymer can comprise a degradable ionene unit 100 (e.g., characterized by chemical formula 500) having antimicrobial functionality. For instance, a carbonyl group can be formed adjacent to one or more amine groups comprising a norspermidine structure of the ionene unit 100, thereby forming an amide group (e.g., as shown in FIG. 5). Thus, the oxidation at 604 can impart one or more carbonyl groups to the dissolved ionene unit 100 (e.g., characterized by chemical formula 200); for example, to generate a degradable (e.g., biodegradable) ionene unit 100 (e.g., characterized by chemical formula 500) without loss to antimicrobial efficacy and/or selectivity. In one or more embodiments, method 600 can generate ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

For example, the ionene formed at 604 can comprise one or more embodiments of the ionene unit 100 and can be characterized by one or more embodiments of chemical formula 500. For instance, the ionene unit 100 formed at 604 can comprise a molecular backbone 102 that can comprise one or more cations 104 (e.g., represented by "X" in chemical formula 200), one or more norspermidine structures, one or more carbonyl groups distributed along the molecular backbone 102, and/or one or more hydrophobic functional groups 106 (e.g., represented by "R" in chemical formula 200). The one or more cations 104 can be nitrogen cations (e.g., protonated secondary amine cations, protonated tertiary amine cations, quaternary ammonium cations, imidazolium cations, and/or a combination thereof). Also, the one or more of the cations 104 can be bonded to one or more of the hydrophobic functional groups 106. Additionally, the ionene unit 100 can comprise a polyionene by repeating a number of times, as represented by "n" in chemical formula 500 (e.g., shown in FIG. 5), which can be an integer greater than or equal to one and less than or equal to one thousand.

Figure 7:
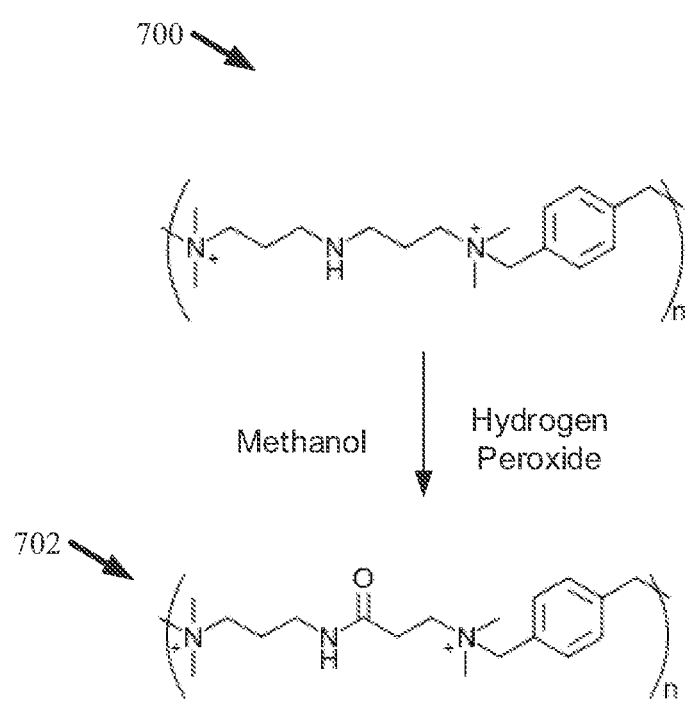
FIG. 7 illustrates a diagram of an example, non-limiting scheme that can depict generating one or more ionene units in accordance with one or more embodiments described herein.

FIG. 7 illustrates a diagram of an example, non-limiting scheme 700 that can depict generating one or more ionene units 100 (e.g., characterized by chemical formula 500) in accordance with one or more of the methods (e.g., method 600) described herein. Repetitive description of like elements employed in other embodiments described herein is omitted for sake of brevity. In scheme 700, "n" can represent a first integer greater than or equal to one and less than or equal to one thousand. Scheme 700 can exemplify one or more ionene units 100 characterized by chemical formula 600 and/or generated by method 500. While one or more particular ionene reactants (e.g., characterized by chemical formula 200), oxidizing agents, and/or solvents are depicted; additional embodiments of scheme 700 are also envisaged. For example, the principal mechanism of scheme 700 can be applied to any ionene reactants (e.g., characterized by chemical formula 200), oxidizing agents, and/or solvents in accordance with the various features described herein (e.g., with reference to chemical formula 500 and/or method 600).

Scheme 700 can depict oxidizing one or more ionene unit 100 (e.g., characterized by chemical formula 200) with an oxidizing agent comprising oxygen (e.g., hydrogen peroxide) in a solvent that comprise one or more alcohol groups (e.g., methanol). FIG. 7 depicts one or more ionene units 100 that can be formed in accordance with scheme 400 and/or method 300 as a reactant in the oxidization. However, other ionene units 100 (e.g., characterized by chemical formula 200) are also envisaged (e.g., ionene units 100 prepared by techniques other than method 300 and/or scheme 400).

To facilitate the oxidizing, the one or more ionene units 100 (e.g. characterized by formula 200), the oxidizing agent (e.g., hydrogen peroxide), and/or the solvent (e.g., methanol) can be stirred at a temperature greater than or equal to 15° C. and less than or equal to 150° C. for a period of time greater than or equal to 8 hours and less than or equal to 72 hours (e.g., greater than or equal to 12 hours and less than or equal to 24 hours).

The oxidation comprising scheme 700 can generate one or more carbonyl groups along one or more molecular backbones 102 of the one or more ionene units 100 (e.g., characterized by chemical formula 200). For example, one or more carbonyl groups can be formed adjacent to one or more amino groups comprising one or more norspermidine structures of the one or more molecular backbones 102, thereby forming one or more amides. The one or more carbonyl groups (e.g., one or more amide groups) can render the one or more ionene units 100 degradable (e.g., biodegradable). Thus, scheme 700 can generate one or more degradable ionene units 100 (e.g., second ionene composition 702). Further, the one or more degradable ionene units 100 can be monomers and/or polymers (e.g., a homopolymer, an alternating copolymer, and/or a random copolymer). In one or more embodiments, scheme 700 can generate ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

Figure 8A:
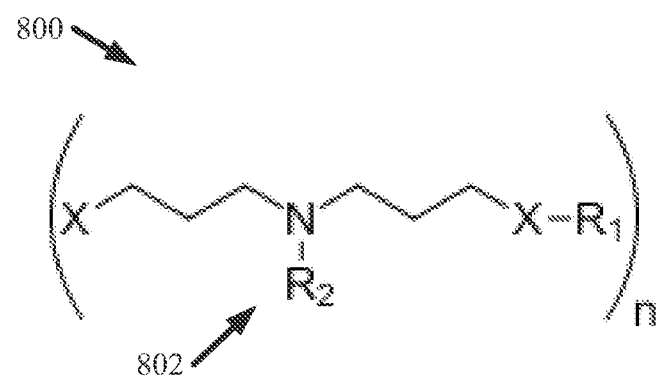
FIG. 8A illustrates a diagram of an example, non-limiting chemical formula that can characterize one or more ionene units in accordance with one or more embodiments described herein.

FIG. 8A illustrates another diagram of an example, non-limiting chemical formula 800 that can characterize the structure of an ionene unit 100 in accordance with one or more embodiments described herein. Repetitive description of like elements employed in other embodiments described herein is omitted for sake of brevity. In various embodiments, the ionene units 100 characterized by chemical formula 800 can be monomers and/or covalently bonded together to form a polymer (e.g., a homopolymer, an alternating copolymer, and/or a random copolymer).

As shown in FIG. 8A, an ionene unit 100 characterized by chemical formula 800 can comprise a molecular backbone 102. Further, the molecular backbone 102 can comprise one or more norspermidine structures. In various embodiments, the ionene unit 100 characterized by chemical formula 800 can be derived from 3.3'-iminobis(N, N-dimethyl propylamine), wherein the one or more norspermidine structures can be derived from the 3.3'-iminobis(N, N-dimethyl propylamine). However, one or more embodiments of chemical formula 800 can comprise a norspermidine structure derived from one or more molecules other than 3.3'-iminobis(N, N-dimethyl propylamine).

The "X" in FIG. 8A can represent the one or more cations 104. For example, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. As shown in FIG. 8A, in various embodiments, one or more ionene units 100 characterized by chemical formula 800 can comprise cations 104 (e.g., represented by "X") at a plurality of locations along the molecular backbone 102. For example, cations 104 can be located at either end of the molecular backbone 102 (e.g., as illustrated in FIG. 8A). However, in one or more embodiments of chemical formula 800, the molecular backbone 102 can comprise less or more cations 104 than the two illustrated in FIG. 8A.

Further, the "$R_1$" shown in FIG. 8A can represent the one or more hydrophobic functional groups 106 in accordance with the various embodiments described herein. For example, the one or more hydrophobic functional groups 106 can comprise one or more alkyl groups and/or one or more aryl groups. For instance, the one or more hydrophobic functional group 106 can be derived from one or more dialkyl halides. The one or more hydrophobic functional groups 106 (e.g., represented by "$R_1$" in FIG. 8) can be covalently bonded to one or more of the cations 104 (e.g., represented by "X" in FIG. 8) and/or the molecular backbone 102.

The "$R_2$" shown in FIG. 8A can represent one or more carbamate functional groups 802. The one or more carbamate functional groups 802 can be derived from one or more carbonates covalently bonded to one or more amino groups of the molecular backbone 102 (e.g., one or more amino groups comprising the one or more norspermidine structures). The one or more carbamate functional groups 802 can comprise chain and/or ring formations. For example, the one or more carbamate functional groups 802 can be derived from one or more cyclic carbonates. Additionally, the one or more carbamate functional groups 802 can be functionalized to comprise one or more hydroxyl groups.

The one or more ionene units 100 characterized by chemical formula 800 can comprise one or more cations 104 (e.g., a protonated secondary amine cation, a protonated tertiary amine cation, a quaternary ammonium cation, and/or an imidazolium cation) distributed along a molecular backbone 102. The molecular backbone 102 can comprise one or more norspermidine structures and can be bonded to one or more carbamate functional groups 802. Further, one or more hydrophobic functional groups 106 can be bonded to the molecular backbone 102 (e.g., bonded to one or more cations 104). Additionally, the one or more ionene units 100 can repeat a number of times designated by "n" in chemical formula 800, wherein "n" can represent an integer greater than or equal to one and less than or equal to one thousand. In one or more embodiments, chemical formula 800 can characterize ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

The one or more ionene units 100 characterized by chemical formula 800 can form monomers and/or polymers (e.g., homopolymers, alternating copolymers, and/or random copolymers). For example, functionalizing an ionene unit 100 (e.g., characterized by chemical formula 200) can generate a degradable ionene unit 100 (e.g., characterized by chemical formula 800) with enhanced mobility (e.g., facilitating the ionene unit's 100 ability to enter and/or exit cells). However, said functionalization can also reduce antimicrobial potency.

Figure 8B:
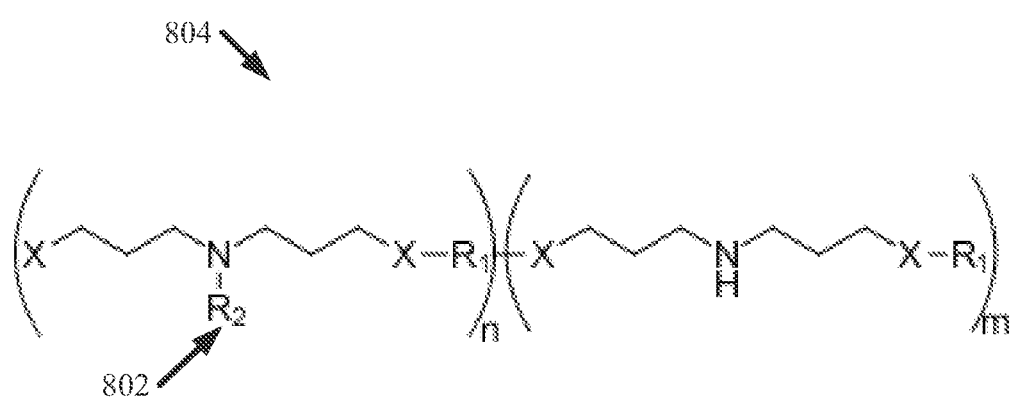
FIG. 8B illustrates a diagram of an example, non-limiting chemical formula that can characterize one or more ionene units in accordance with one or more embodiments described herein.

FIG. 8B illustrates a diagram of an example, non-limiting chemical formula 804 that can characterize one or more copolymers comprising varying ionene units 100 in accordance with the embodiments described herein. Repetitive description of like elements employed in other embodiments described herein is omitted for sake of brevity. In chemical formula 804, "n" can represent an integer greater than or equal to one and less than or equal to one thousand. Also, "m" can represent an integer greater than or equal to one and less than or equal to one thousand. As shown in FIG. 8B, chemical formula 804 can characterize one or more copolymer polyionenes comprising a first ionene unit 100 that can be characterized by chemical formula 800 bonded to a second ionene unit 100 that can be characterized by chemical formula 200. Chemical formula 804 can regard an alternating copolymer composition and/or a random copolymer composition. In one or more embodiments, chemical formula 804 can characterize ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

Figure 8C:
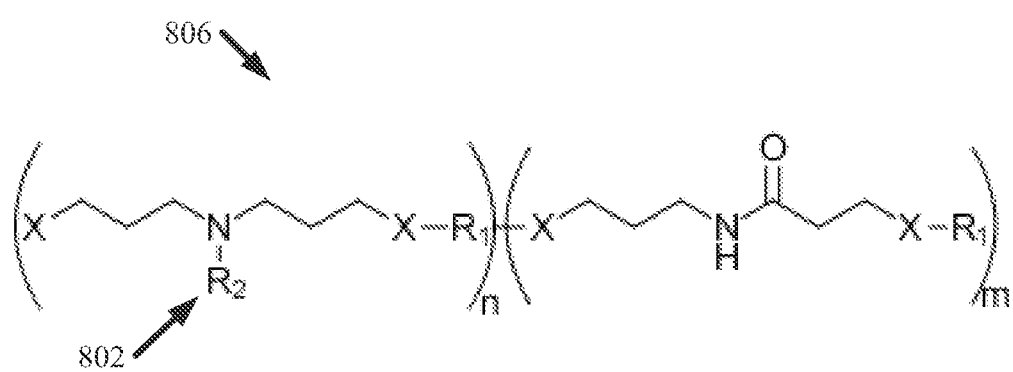
FIG. 8C illustrates a diagram of an example, non-limiting chemical formula that can characterize one or more ionene units in accordance with one or more embodiments described herein.

FIG. 8C illustrates a diagram of an example, non-limiting chemical formula 806 that can characterize one or more copolymers comprising varying ionene units 100 in accordance with the embodiments described herein. Repetitive description of like elements employed in other embodiments described herein is omitted for sake of brevity. In chemical formula 806, "n" can represent an integer greater than or equal to one and less than or equal to one thousand. Also, "m" can represent an integer greater than or equal to one and less than or equal to one thousand. As shown in FIG. 8C, chemical formula 806 can characterize one or more copolymer polyionenes comprising a first ionene unit 100 that can be characterized by chemical formula 800 bonded to a second ionene unit 100 that can be characterized by chemical formula 500. Chemical formula 806 can regard an alternating copolymer composition and/or a random copolymer composition. Chemical formula 806 can depict an antimicrobial copolymer that can be degradable, at least partially due to the structure characterized by chemical formula 500, and/or can exhibit enhanced functionality (e.g., lower toxicity and/or increased intra-cell mobility), at least partially due to the structure characterized by chemical formula 800. In one or more embodiments, chemical formula 806 can characterize ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

Figure 9:
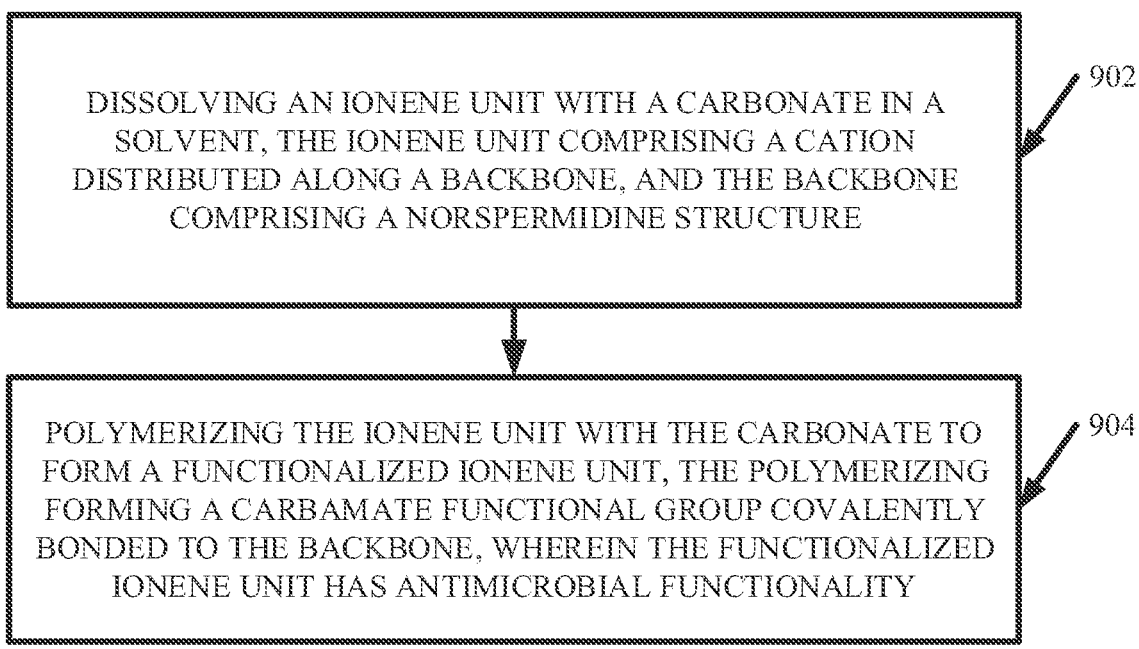
FIG. 9 illustrates a flow diagram of an example, non-limiting method that can facilitate generating one or more ionene units in accordance with one or more embodiments described herein.

FIG. 9 illustrates another flow diagram of an example, non-limiting method 900 that can facilitate generating one or more ionene units 100 (e.g., characterized by chemical formula 800 and/or 804) in accordance with one or more embodiments described herein. Repetitive description of like elements employed in other embodiments described herein is omitted for sake of brevity. In one or more embodiments, the one or more ionene units 100 utilized as reactants in method 900 can be characterized by chemical formula 200 and/or can be prepared in accordance with the various features of method 300. In various embodiments, the one or more ionene units 100 utilized as reactants in method 900 can be characterized by chemical formula 500 and/or prepared in accordance with the various features of method 600. In some embodiments, the one or more ionene units 100 utilized as reactants in method 900 can be characterized by chemical formula 200 and/or 500 and/or can be prepared in accordance with the various features of method 300 and/or 600. However, one or more ionene units 100 prepared by alternative means can also be utilized as reactants in method 900.

At 902, the method 900 can comprise dissolving one or more ionene units 100 with one or more carbonates in a solvent. The one or more ionene units 100 can be characterized by chemical formula 200. Also, the one or more ionene units 100 can comprise one or more cations 104 distributed along a molecular backbone 102. For example, the one or more cations 104 can be protonated secondary amine cations, protonated tertiary amine cations, quaternary ammonium cations, and/or imidazolium cations. The molecular backbone 102 can comprise one or more norspermidine structures. For example, the one or more ionene units 100 can be a tri-amines. Additionally, one or more hydrophobic functional groups 106 can be covalently bonded to the molecular backbone 102 (e.g., bonded to the one or more cations 104).

The one or more carbonates can comprise one or more chain formations and/or one or more ring formations. Also, the one or more carbonates can comprise one or more alkyl groups, one or more aryl groups, one or more carboxyl groups, one or more ester groups, one or more ether groups, one or ketone groups, one or more aldehyde groups, a combination thereof, and/or the like. For example, the one or more carbonates can be cyclic carbonates. Further, the solvent can be an organic solvent. Additionally, the solvent can be an aprotic solvent, a dipolar solvent, and/or an alcohol. Example solvents can include but are not limited to: DMF, methanol, and/or a combination thereof, and/or the like.

To facilitate the dissolving, the method 900 can further comprise stirring the one or more ionene units 100, the one or more carbonates, and/or the solvent at a temperature greater than or equal to 15° C. and less than or equal to 150° C. for a period of time greater than or equal to 8 hours and less than or equal to 72 hours (e.g., greater than or equal to 12 hours and less than or equal to 24 hours).

At 904, the method 900 can comprise polymerizing the one or more ionene units 100 (e.g., characterized by chemical formula 200 and/or 500) with the one or more carbonates to form a polymer (e.g., a homopolymer, an alternating copolymer, and/or a random copolymer). The polymerizing at 904 can form one or more carbamate functional groups 802 distributed along the one or more molecular backbones 102 of the one or more ionene units 100. The one or more carbamate functional groups 802 can be formed by covalently bonding one or more carbonates to one or more amino groups of the one or more ionene units 100 (e.g., characterized by chemical formula 200 and/or 500). For example, one or more carbonates can bond to one or more secondary amino groups comprising one or more norspermidine structures in the one or more molecule backbones 102. Additionally, the polymerizing at 904 can comprise a ring-opening polymerization (ROP). For example, the polymerizing at 904 can comprise a ROP that covalently bones one or more cyclic carbonates to one or more amino groups (e.g., secondary amino groups) comprising one or more norspermidine structures along the one or more molecular backbones 102 in order to form one or more carbamate functional groups 802. Thus, the polymer formed at 904 can comprise a degradable (e.g., biodegradable) ionene unit 100 (e.g., characterized by chemical formula 800 and/or 804) having antimicrobial functionality. In one or more embodiments, method 900 can generate ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

For example, the polymer can be a homopolymer, an alternating copolymer, and/or a random copolymer. For example, the polymer can be characterized by chemical formula 800, 804, and/or 806. Also, the polymer can comprise one or more cations 104 (e.g., a protonated secondary amine cation, a protonated tertiary amine cation, a quaternary ammonium cation, and/or an imidazolium cation) distributed along a molecular backbone 102. The molecular backbone 102 can comprise one or more norspermidine structures and can be bonded to one or more carbamate functional groups 802. Further, one or more hydrophobic functional groups 106 can be bonded to the molecular backbone 102 (e.g., bonded to one or more cations 104). Additionally, the one or more ionene units 100 can repeat a number of times designated by "n" in chemical formulas 800 and/or 804, wherein "n" can represent an integer greater than or equal to one and less than or equal to one thousand.

Figure 10:
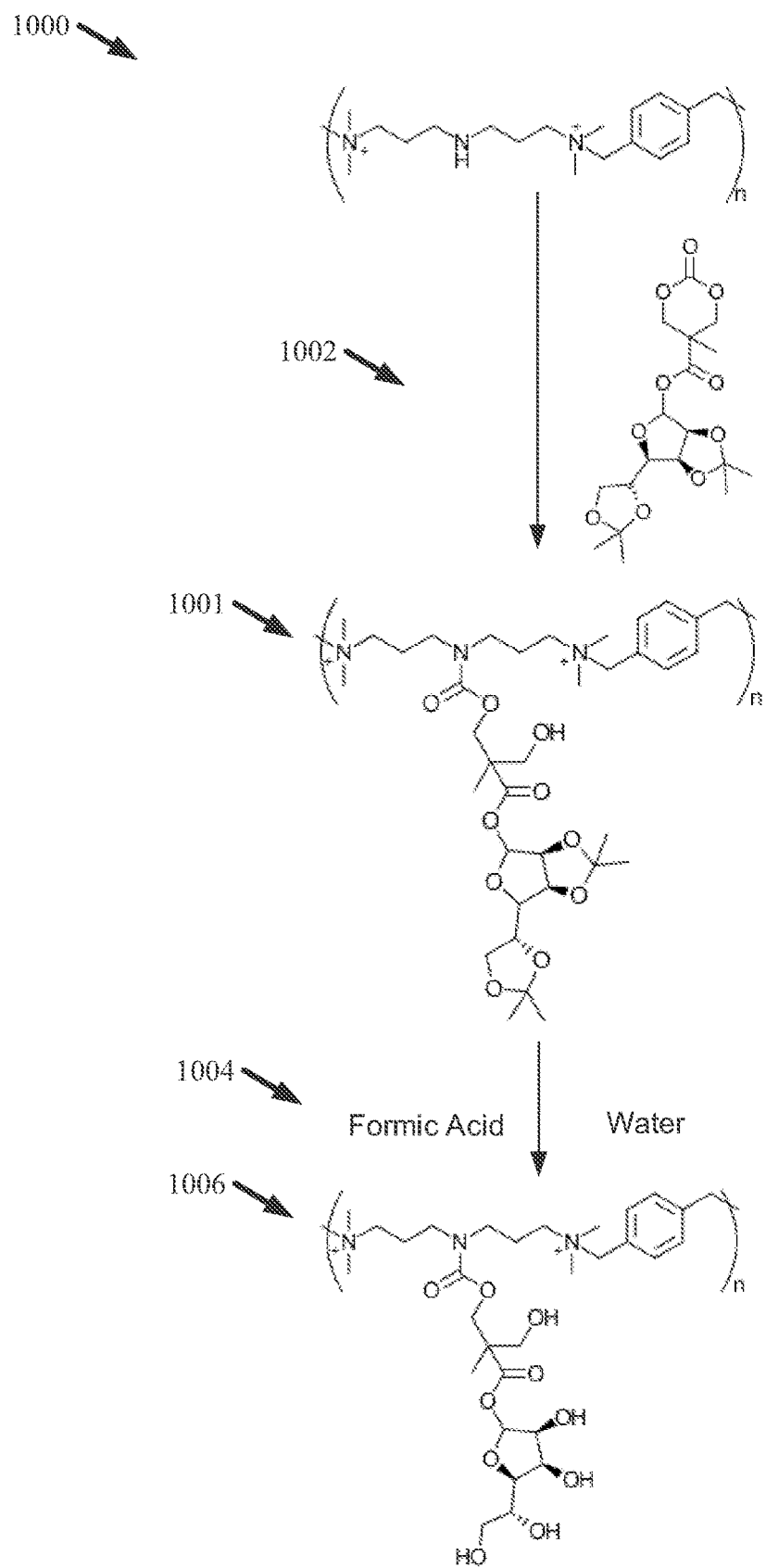
FIG. 10 illustrates a diagram of an example, non-limiting scheme that can depict generating one or more ionene units in accordance with one or more embodiments described herein.

FIG. 10 illustrates a diagram of an example, non-limiting scheme 1000 that can depict generating one or more ionene units 100 (e.g., characterized by chemical formula 800, 804, and/or 806) in accordance with one or more of the methods (e.g., method 900) described herein. Repetitive description of like elements employed in other embodiments described herein is omitted for sake of brevity. In scheme 1000, "n" can represent a first integer greater than or equal to one and less than or equal to one thousand. Scheme 1000 can exemplify one or more ionene units 100 characterized by chemical formula 800, 804, and/or 806 and/or generated by method 900. While one or more particular ionene reactants (e.g., characterized by chemical formula 200 and/or chemical formula 500), carbonates, acids, and/or solvents are depicted; additional embodiments of scheme 1000 are also envisaged. For example, the principal mechanisms of scheme 1000 can be applied to any ionene reactants (e.g., characterized by chemical formula 200 and/or chemical formula 500), carbonates, acids, and/or solvents in accordance with the various features described herein (e.g., with reference to chemical formula 800 and/or 804 and/or method 900).

At 1002, scheme 1000 can depict polymerizing one or more ionene units 100 (e.g., characterized by chemical formula 200) with one or more carbonates in a solvent (e.g., "DMF") to form one or more ionene compositions (e.g., third ionene composition 1001). FIG. 10 depicts one or more ionene units 100 that can be formed in accordance with scheme 400 and/or method 300 as a reactant in the polymerization. However, other ionene units 100 (e.g., characterized by chemical formula 200) are also envisaged (e.g., ionene units 100 prepared by techniques other than method 300 and/or scheme 400).

To facilitate the polymerization, the one or more ionene units 100 (e.g. characterized by formula 200), the one or more carbonates (e.g., as shown in FIG. 10), and/or the solvent (e.g., DMF) can be stirred at a temperature greater than or equal to 15° C. and less than or equal to 150° C. for a period of time greater than or equal to 8 hours and less than or equal to 72 hours (e.g., greater than or equal to 12 hours and less than or equal to 24 hours).

The polymerization at 1002 can generate one or more carbamate functional groups 802 bonded to one or more molecular backbones 102. For example, the polymerization can comprise a ROP to bond the one or more carbonates to one or more amino groups comprising the one or more molecular backbones 102 (e.g., comprising one or more norspermidine structures).

At 1004, scheme 1000 can further comprise depolymerizing the one or more intermediate ionene units 100 formed at 1002 with an acid (e.g., formic acid) in a solvent (e.g., water) to form another ionene composition (e.g., fourth ionene composition 1006). The depolymerizing can open one or more rings of the one or more carbamate functional groups 802 formed at 1002, thereby forming one or more hydroxyl groups along a structure of the one or more carbamate functional groups 802. The ionene composition (e.g., third ionene composition 1001 and/or fourth ionene composition 1006) can be a degradable (e.g., biodegradable) ionene monomer and/or polyionene polymer (e.g., a homopolymer, an alternating copolymer, and/or a random copolymer). In one or more embodiments, scheme 1000 can generate ionene and/or polyionene compositions having a molecular weight greater than or equal to 3,000 g/mol and less than or equal to 10,000 g/mol (e.g., greater than or equal to 4,000 g/mol and less than or equal to 7,000 g/mol).

Figures 11A, 11B:
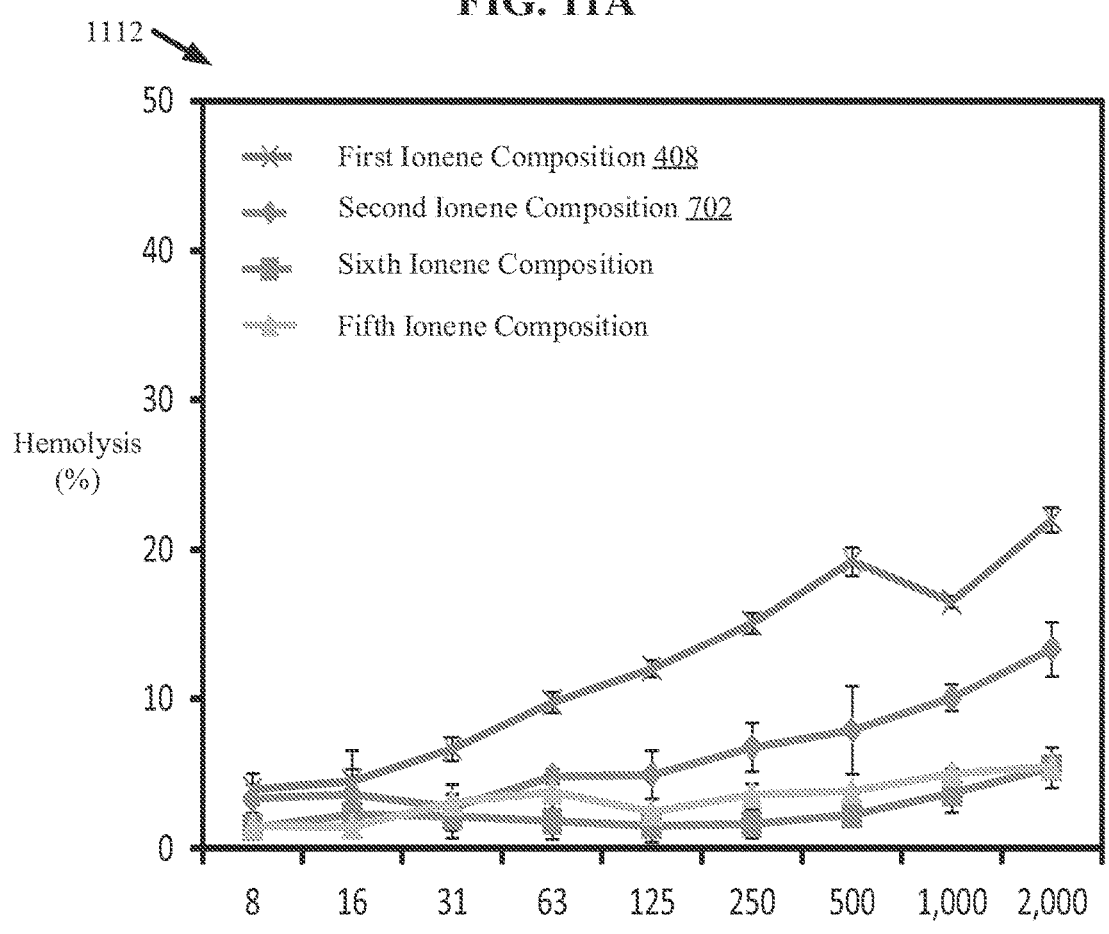
FIG. 11A illustrates a diagram of an example, non-limiting chart that can depict the antimicrobial functionality of one or more ionene compositions in accordance with one or more embodiments described herein.
FIG. 11B illustrates a diagram of an example, non-limiting chart that can depict the antimicrobial functionality of one or more ionene compositions in accordance with one or more embodiments described herein.

FIG. 11A illustrates a diagram of an example, non-limiting chart 1100 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ioenene compositions described herein (e.g., comprising ionene units 100 that can be: characterized by chemical formula 200, chemical formula 500, chemical formula 800, and/or chemical formula 804; generated by method 300, method 600, and/or method 900; and/or depicted in scheme 400, scheme 700, scheme 500, and/or scheme 1000), a plurality of ionene compositions were evaluated against a broad spectrum of pathogens.

The first column 1102 of chart 1100 can depict the ionene compositions subject to evaluation. For example, the first column 1102 can include first ionene composition 408 and/or second ionene composition 702. The first ionene composition 408 can have a molecular weight of 5,210 g/mol and/or a polydispersity index (PDI) of 1.69. Also, the second ionene composition 702 can have a molecular weight of 4,640 g/mol and/or a PDI of 1.72.

Furthermore, the first column 1102 can include a fifth ionene composition that can be characterized by the formula 1:

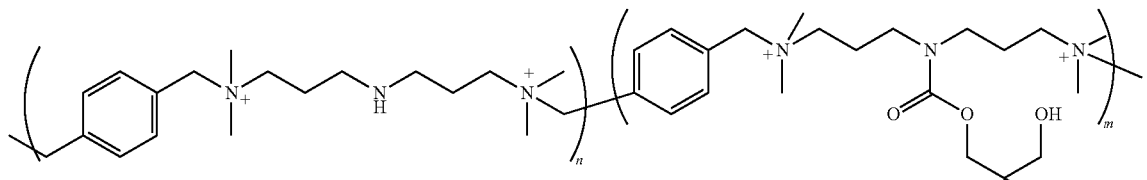

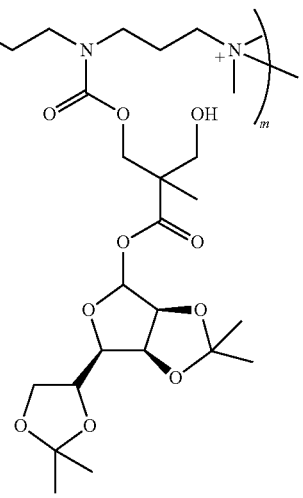

As shown in formula 1, "n" can represent a first integer greater than or equal to one and less than or equal to one thousand. Also, "m" can represent a second integer greater than or equal to one and less than or equal to one thousand. A ratio of "m" to "n" can be 2:1 The fifth ionene composition can have a molecular weight of 4,110 g/mol and/or a PDI of 1.78.

Moreover, the first column 1102 can include a sixth ionene composition that can be characterized by formula 2:

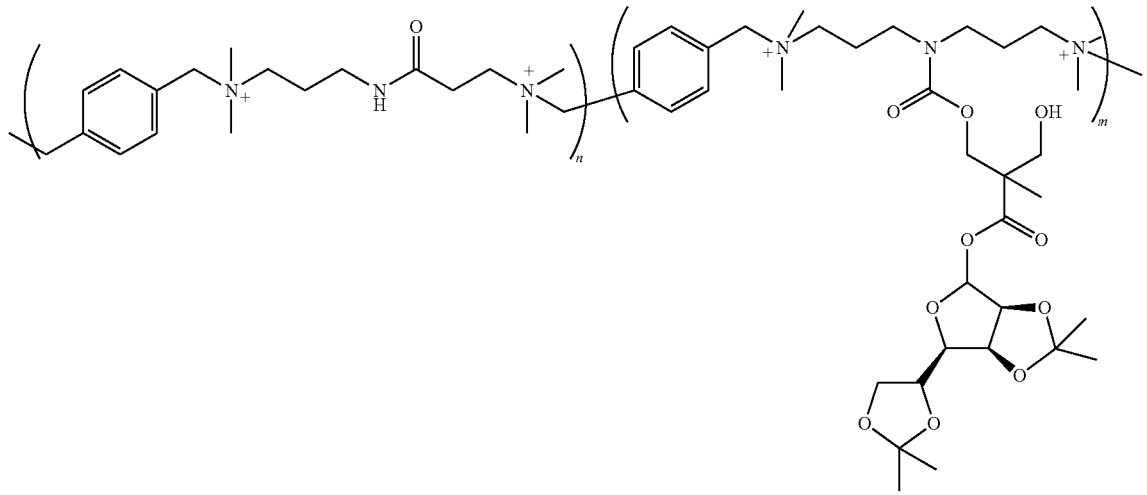

As shown in formula 2, "n" can represent a first integer greater than or equal to one and less than or equal to one thousand. Also, "m" can represent a second integer greater than or equal to one and less than or equal to one thousand. A ratio of "m" to "n" can be 2:1 The sixth ionene composition can have a molecular weight of 3,730 g/mol and/or a PDI of 1.79. Formula 1 and/or formula 2 both characterize structures that can be generated in accordance with method 900 and/or scheme 1000.

The second column 1104 of chart 1100 can depict the minimum inhibitory concentration (MIC) in micrograms per milliliter (μg/mL) of the subject polymer composition regarding *Staphylococcus aureus* ("SA"). The third column 1106 of chart 1100 can depict the MIC in μg/mL of the subject polymer composition regarding *Escherichia coli* ("EC"). The fourth column 1108 of chart 1100 can depict the MIC in μg/mL of the subject polymer composition regarding *Pseudomonas aeruginosa* ("PA"). The fifth column 1110 of chart 1100 can depict the MIC in μg/mL of the subject polymer composition regarding *Candida albicans* ("CA"). Chart 1100 can demonstrate that the various embodiments described herein can describe and/or generate ionene compositions that have strong antimicrobial potency.

FIG. 11B illustrates a diagram of an example, non-limiting graph 1112 that can depict the hemolytic activity of various ionene compositions at various concentrations in accordance with the one or more embodiments described herein. Repetitive description of like elements employed in other embodiments described herein is omitted for sake of brevity. For example, FIG. 11B shows the hemolytic activity of the first ionene composition 408, the second ionene composition 702, the fifth ionene composition (e.g., characterized by formula 1), and/or the sixth ionene composition (e.g., characterized by formula 2) at concentrations ranging from 8 parts per million (ppm) to 2000 ppm. The hemolytic activity depicted in graph 1112 can regard rat red blood cells.

Figure 12:
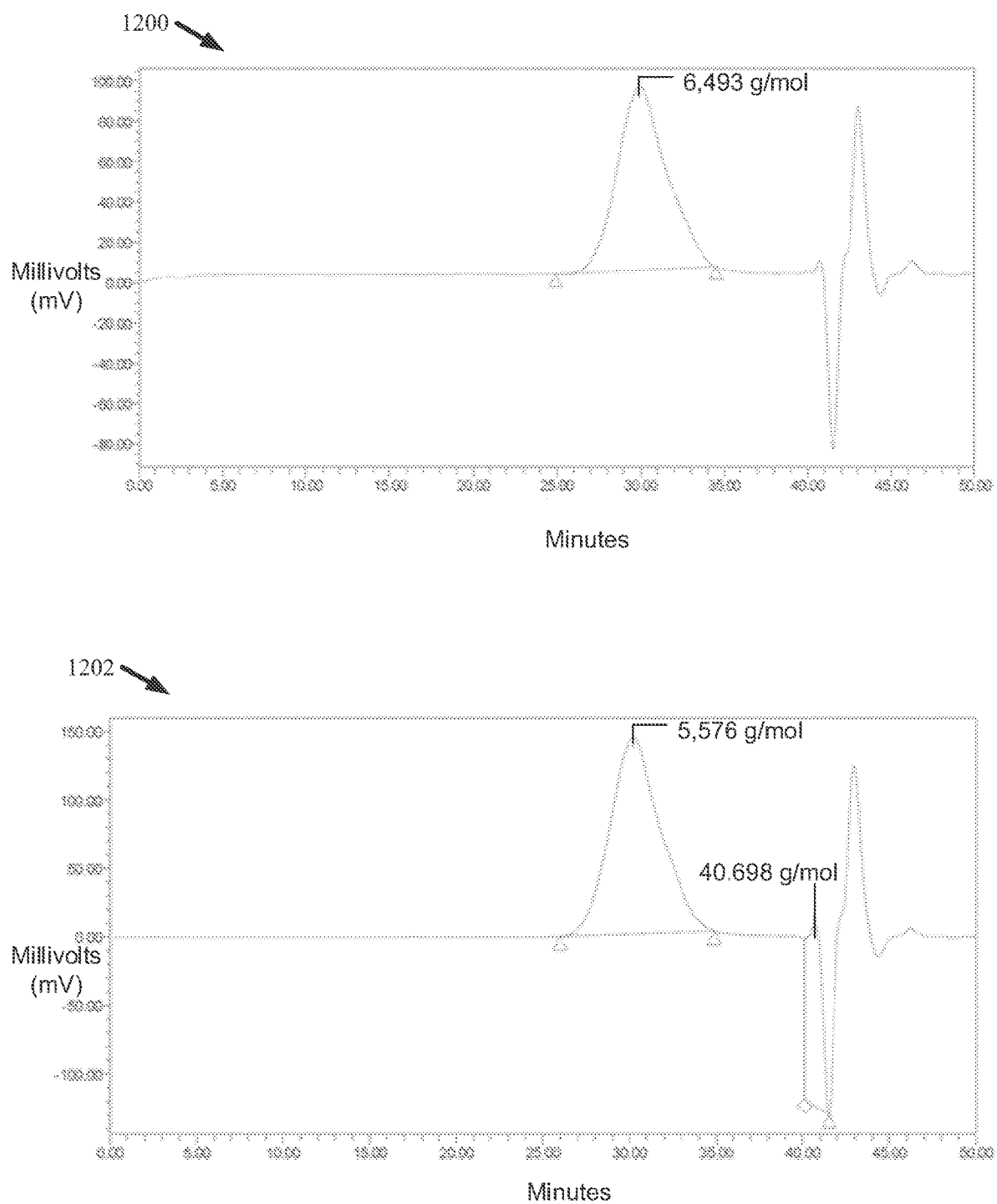
FIG. 12 illustrates a diagram of example, non-limiting graphs that can depict molecular weight characteristics of one or more ionene compositions in accordance with one or more embodiments described herein.

FIG. 12 illustrates a diagram of example, non-limiting graph 1200 and/or graph 1202 that can depict molecular weight characteristics regarding a plurality of ioenene compositions in accordance with one or more embodiments described herein. Repetitive description of like elements employed in other embodiments described herein is omitted for sake of brevity.

Graph 1200 can depict a gel permeation chromatography (GPC) graph regarding an ionene composition (e.g. that can be characterized by chemical formula 500 and generated in accordance with method 600 and/or scheme 700) that can comprise an average molecular weight ($M_n$) of 4,114 g/mol, a weight average molecular weight ($M_w$) of 6,651 g/mol, and/or a polydispersity index (PDI) of 1.62. Graph 1202 can depict a GPC graph regarding another ionene composition (e.g. that can be characterized by chemical formula 500 and generated in accordance with method 600 and/or scheme 700) that can comprise a $M_n$ of 3,760 g/mol, a $M_w$ of 6,063 g/mol, and/or a PDI of 1.61.

FIG. 13 illustrates another flow diagram of an example, non-limiting method 1300 of killing a pathogen, preventing the growth of a pathogen, and/or preventing contamination by a pathogen. Repetitive description of like elements employed in other embodiments described herein is omitted for sake of brevity. Example pathogens include, but are not limited to: Gram-negative bacteria, Gram-positive bacteria, fungi, yeast, a combination thereof, and/or the like.

At 1302, the method 1000 can comprise contacting the pathogen with a polymer. The polymer can comprise an ionene unit 100 (e.g., characterized by chemical formula 200, 500, 800, 804, and/or 806). The ionene unit 100 can comprise a cation 104 (e.g., a nitrogen cation cation) distributed along a degradable molecular backbone 102 that can comprise one or more norspermidine structures (e.g., derived from 3.3'-iminobis(N, N-dimethyl propylamine)). The ionene unit 100 can have antimicrobial functionality. Additionally, the ionene unit 100 can have an amide group distributed along the molecular backbone 102. For example, the amide group can be included in a carbonyl group distributed along the molecular backbone 102 and/or a carbamate functional group 802 bonded to the molecular backbone 102.

At 1304, the method 1300 can comprise electrostatically disrupting a membrane of the pathogen (e.g., via lysis process 108) upon contacting the pathogen with the polymer (e.g., an ionene unit 100 characterized by chemical formula 200, 500, 800, 804, and/or 806). Additionally, contacting the pathogen with the polymer (e.g., ionene unit 100 characterized by chemical formula 200, 500, 800, 804, and/or 806) can disrupt the membrane through hydrophobic membrane integration (e.g., via lysis process 108).

The ionene unit 100 that can comprise the polymer contacting the pathogen at 1302 can comprise one or more embodiments of the ionene unit 100 and can be characterized by one or more embodiments of chemical formula 200, 500, 800, 804, and/or 806. For instance, the ionene unit 100 can comprise a molecular backbone 102 that can comprise one or more cations 104 (e.g., represented by "X" in chemical formula 200, 500, 800, 804, and/or 806), one or more norspermidine structures (e.g., as shown in FIGS. 2, 4-5, 7-8, and 10), which can comprise one or more carbonyl groups (e.g., as shown in FIGS. 5, 7, and/or 8), and/or one or more hydrophobic functional groups 106 (e.g., represented by "R" in chemical formula 200, 500, 800, 804, and/or 806). The one or more cations 104 can be nitrogen cations (e.g., quaternary ammonium cations, imidazolium cations, and/or a combination thereof) and/or phosphorus cations (e.g., quaternary phosphonium cations). Further, one or more of the cations 104 can be bonded to one or more of the hydrophobic functional groups 106. Moreover, one or more carbamate functional groups 802 can be bonded to the molecular backbone 102. Additionally, the ionene unit 100 can repeat a number of times greater than or equal to 1 and less than or equal to 1000. Therefore, the ionene unit 100 contacting the pathogen at 1302 can comprise any and all the features of various embodiments described herein.

The various structures (e.g., described regarding FIGS. 2, 5, and/or 8), compositions (e.g., described regarding FIGS. 4, 7, and/or 10-12), and/or methods (e.g., described regarding FIGS. 3, 6, 9, and/or 13) described herein can be incorporated into a variety of applications. For example, said applications can include cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), and/or the like. In a further example, said applications can include agricultural sprays and/or aqueous solutions that can facilitate processing crops for consumption.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical compound comprising:
an ionene unit comprising a plurality of nitrogen cations distributed along a molecular backbone, the molecular backbone comprising a norspermidine structure, wherein the ionene unit has antimicrobial functionality, and wherein the ionene unit is characterized by a formula:

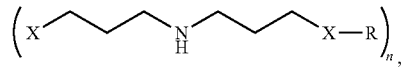

wherein X represents the plurality of nitrogen cations, wherein R represents a hydrophobic aryl functional group, and wherein n represents an integer greater than or equal to one and less than or equal to one thousand.

2. The chemical compound of claim 1, wherein the ionene unit has a structure characterized by a formula:

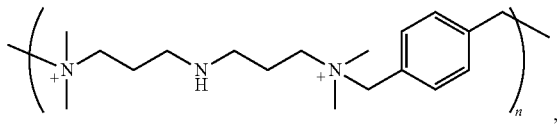

wherein then represents the integer greater than or equal to one and less than or equal to one thousand.

* * * * *